US009872991B2

(12) United States Patent
Bleich et al.

(10) Patent No.: US 9,872,991 B2
(45) Date of Patent: *Jan. 23, 2018

(54) COORDINATING MUSCULOSKELETAL AND CARDIOVASCULAR HEMODYNAMICS

(71) Applicant: Pulson, Inc., Palo Alto, CA (US)

(72) Inventors: Jeffery L. Bleich, Palo Alto, CA (US); Paul Mannheimer, Palo Alto, CA (US); Darin Howard Buxbaum, Palo Alto, CA (US)

(73) Assignee: Pulson, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/278,617

(22) Filed: Sep. 28, 2016

(65) Prior Publication Data

US 2017/0014633 A1 Jan. 19, 2017

Related U.S. Application Data

(63) Continuation of application No. 14/216,960, filed on Mar. 17, 2014, now Pat. No. 9,457,190.

(60) Provisional application No. 61/798,799, filed on Mar. 15, 2013.

(51) Int. Cl.
*A61N 1/365* (2006.01)

(52) U.S. Cl.
CPC ..... *A61N 1/36585* (2013.01); *A61N 1/36507* (2013.01); *A61N 1/36542* (2013.01)

(58) Field of Classification Search
CPC ............ A61N 1/36585; A61N 1/36542; A61N 1/36514; A61N 1/36535
See application file for complete search history.

(56) References Cited

U.S. PATENT DOCUMENTS

| 2,690,174 A | 3/1949 | Fuchs |
| 3,303,841 A | 2/1967 | Dennis |
| 4,253,254 A | 3/1981 | Gill |
| 4,541,417 A | 9/1985 | Krikorian |

(Continued)

FOREIGN PATENT DOCUMENTS

| EP | 2744403 | 6/2014 |
| EP | 2967401 | 1/2016 |

(Continued)

OTHER PUBLICATIONS

International Preliminary Report on Patentability and Written Opinion, received in PCT/US2012/051511, dated Feb. 25, 2014.

(Continued)

*Primary Examiner* — George Evanisko
(74) *Attorney, Agent, or Firm* — Ashley Sloat; Aurora Consulting LLC

(57) ABSTRACT

The present invention is generally directed to methods, systems, and computer program products for coordinating musculoskeletal and cardiovascular hemodynamics. In some embodiments, a heart pacing signal causes heart contractions to occur with an essentially constant time relationship with respect to rhythmic musculoskeletal activity. In other embodiments, prompts (e.g., audio, graphical, etc.) are provided to a user to assist them in timing of their rhythmic musculoskeletal activity relative to timing of their cardiovascular cycle. In further embodiments, accurately indicating a heart condition during a cardiac stress test is increased.

11 Claims, 17 Drawing Sheets

(56) References Cited

U.S. PATENT DOCUMENTS

| | | | |
|---|---|---|---|
| 4,867,442 | A | 9/1989 | Matthews |
| 5,137,501 | A | 8/1992 | Mertsesdorf |
| 5,156,147 | A | 10/1992 | Warren |
| 5,423,869 | A | 6/1995 | Poore |
| 5,462,504 | A | 10/1995 | Trulaske |
| 5,571,075 | A | 11/1996 | Bullard |
| 5,697,884 | A | 12/1997 | Francischelli |
| 6,132,337 | A | 10/2000 | Krupka |
| 6,155,976 | A | 12/2000 | Sackner |
| 6,261,236 | B1 | 7/2001 | Grimblatov |
| 6,261,250 | B1 | 7/2001 | Phillips |
| 6,537,229 | B1 | 3/2003 | Wang |
| 6,556,866 | B2 | 4/2003 | Dal Molin |
| 6,605,046 | B1 | 8/2003 | Del Mar |
| 7,643,873 | B2 | 1/2010 | Chan |
| 7,846,104 | B2 | 12/2010 | Macquarrie et al. |
| 7,908,013 | B2 | 3/2011 | Miesel |
| 8,961,185 | B2 | 2/2015 | Bleich et al. |
| 9,457,190 | B2 | 10/2016 | Bleich et al. |
| 9,522,317 | B2 | 12/2016 | Bleich et al. |
| 2004/0072133 | A1 | 4/2004 | Kullok |
| 2004/0077954 | A1 | 4/2004 | Oakley |
| 2007/0219059 | A1 | 9/2007 | Schwartz et al. |
| 2008/0165017 | A1 | 7/2008 | Schwartz |
| 2008/0236369 | A1 | 10/2008 | Sasaki |
| 2009/0036938 | A1 | 2/2009 | Shipley |
| 2009/0076341 | A1 | 3/2009 | James et al. |
| 2010/0189209 | A1 | 7/2010 | O'Rouke |
| 2013/0103108 | A1* | 4/2013 | Koh .................. A61N 1/36542 607/19 |
| 2015/0080746 | A1 | 3/2015 | Bleich et al. |
| 2016/0148531 | A1 | 5/2016 | Bleich et al. |
| 2017/0014633 | A1 | 1/2017 | Bleich et al. |

FOREIGN PATENT DOCUMENTS

| | | |
|---|---|---|
| WO | WO2013028581 | 2/2013 |
| WO | WO2014145863 | 9/2014 |
| WO | WO2016053793 | 4/2016 |
| WO | WO2016085768 | 6/2016 |

OTHER PUBLICATIONS

International Preliminary Report on Patentability and Written Opinion, received in PCT/US2014/030699, dated Sep. 15, 2015.
Coleman, W., "On the Correlation of the Rate of Beat, Breathing, Bodily Movement Sensory Stimuli", J. Physiol, vol. 54, No. 4, pp. 213-217, Dec. 7, 1920.
Coleman, W., "The Psychological Significance of Bodily Rhythms", The Journal of Comparative Physiology, vol. 1, pp. 213-220, 1921.
Heagerty, A., "Winning rhythm?", The Lancet, vol. 343, pp. 310, Feb. 5, 1994.
Kirby, et al., "Coupling of Cardiac and Locomotor Rhythms", American Physiological Society, 0161-7567/89, pp. 323-329, 1989.
McDonald, D., "Regional Pulse-Wave Velocity in the Arterial Tree", J. Applied Physiology, vol. 24, No. 1, pp. 73-78. 1968.
Murry et al., "Preconditioning with Ischemia: a delay of lethal cell injury in ischemic myocardium", Circulation, vol. 74, No. 5, pp. 1124-1136, 1986.
T. Nakazumi et al., Entrainment of the heart beat into the running pitch during endurance running [I], Japanese J Phys Fitness and Sports Med 1986, vol. 36 No. 6, p. 340.
Nichols et al., "McDonald's Blood Flow in Arteries", Chapter 25 "Exercise", pp. 452-498, Hodder Arnold Publishers, Apr. 28, 2005.
Niizeki et al., "Phase-Dependent Heartbeat Modulation by Muscle Contractions During Dynamic Handgrip in Humans", American Physiolofical Society, 0363-6135/99, pp. H1331-H1338, 1999.
Niizeki K., "Intramuscular pressure-induced inhibition of cardiac contraction: implications for cardiac locomotor synchronization", Am J Physiol Regul Integr Comp Physiol 288: R645-R650, 2005 (First published Nov. 4, 2004; doi:10.1152/ajpregu.00491, 2004).
Nomura, et al., "Analysis entrainment of cardia and locomotor rhythms in humans using the surrogate data technique", European Journal of Applied Physiology, vol. 84, No. 5, pp. 373-378, 2001.
Nomura, et al., "Phase-dependent chronotropic response of the heart during running in humans", Eur J Appl Physiol vol. 97, pp. 240-247, 2006.
O'Rourke et al., "Improved cardiovascular performance with optimal entrainment between heart rate and step rate during running in human," Coronary Artery Disease vol. 3, pp. 863-869, 1992.
O'Rourke et al., "The rhythm of running: can the heart join in?", Aust NZ J Med, vol. 23, pp. 708-710, 1993.
Palatini et al., "Blood pressure changes during running in humans: the 'beat' phenomenon", American Physiological Society, 0161-7567, 1989.
M. Udo, et al., Entrainment of the heart beat into the running pitch during endurance running [II], Japanese J Phys Fitness and Sports Med 1986, vol. 36, No. 6, p. 341.
D. Zhang, An experimental and modeling study of the relationship between step rate and heart rate during running exercise, Doctorate Thesis, University of New South Wales, Sidney, Australia, 2002.
Zhang et al., "Possible mechanism for modulating cardiovascular system during running in humans", 23rd Annual International Conference of the IEEE Engineering in Medicine and Biology Society, Oct. 25-26, 2001.
Zhang et al., "Monitoring Physiological Signals during Running Exercise", 23rd Annual International Conference of the IEEE Engineering in Medicine and Biology Society, Oct. 25-26, 2001.
D. Zhang et al., "The effect of heartbeat-synchronised running on the cardiovascular system," Conference Proceedings, 2nd Joint EMBS-BMES Conference 2002, 24th Annual International Conference of the Engineering in Medical and Biology Society, Annual Fall meeting of the Biomedical Engineering Society, IEEE, vol. 2, 2002, pp. 1295-1296.
Zhao et al., "Inhibition of myocardial injury by ischemic postconditioning during reperfusion: comparison with ischemic preconditioning", Am J Physiol Heart Circ Physiol 285: H579-H588, 2003 (first published Apr. 3, 2003; 10,1152/ajpheart.01069, 2002).
International Search Report received in PCT/US2015/052326, dated Dec. 23, 2015.
International Search Report and Written Opinion received in PCT/US2015/061696, dated Feb. 2, 2016.
First Exam Report (EPO Form 2906) issued in Application No. 12 754 154.8 dated Jun. 26, 2015.

* cited by examiner

COORDINATING MUSCULOSKELETAL AND CARDIOVASCULAR HEMODYNAMICS

CROSS-REFERENCE TO RELATED APPLICATIONS

This application is a continuation of U.S. patent application Ser. No 14/216,960, entitled "Coordinating Musculoskeletal and Cardiovascular Hemodynamics," filed Mar. 17, 2014, which claims the benefit of and priority to U.S. Provisional Patent Application Ser. No. 61/798,799, entitled "Systems And Methods For Reliably Coordinating Musculoskeletal And Cardiovascular Hemodynamics", filed Mar. 15, 2013, each of which is incorporated herein by reference in its entirety.

COPYRIGHT NOTICE

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND

1. Field of the Invention

This invention relates generally to the field of human physiology, and, more particularly, to methods, apparatus, systems, and computer program products for coordinating musculoskeletal and cardiovascular hemodynamics.

2. Related Art

Blood is circulated through the body by the heart during its rhythmic pumping cycle, which consists of two distinct periods—systole and diastole. Heart muscle (myocardium) contracts to eject blood from the ventricles during the systolic period of each cardiac cycle (CC). Ejection of blood from the ventricles generates arterial blood pressure and flow adequate to deliver blood throughout the body, thereby transporting oxygen, nutrients and metabolic products, removing carbon dioxide and waste, and facilitating critical physiological functions such as heat exchange. The heart subsequently relaxes during the diastolic period of the CC, when the atrial and ventricular chambers refill with blood in preparation for the heart's next contraction.

Unlike the rest of the body, which receives most of its blood flow as a result of pressure generated during systole, the heart's own arterial blood supply is delivered primarily during the diastolic portion of the cycle when the heart muscle is relaxing and the heart chambers are filling for the next contraction. Little blood flows to perfuse the myocardium during systole because the heart's contraction generates high forces within its muscular walls and thereby prevents flow through the coronary blood vessels that travel across and through the myocardium. During diastole, when the heart muscle has relaxed, residual blood pressure in the aorta drives blood flow through the coronary arteries and into the myocardial muscle, supplying the heart with its needed oxygen and nutrients.

In addition to the heart's pumping function, the musculoskeletal (MSK) system also plays an important role in circulating blood throughout the body during physical activity. Arterial and venous blood is pumped rhythmically throughout the body via transient changes in peripheral vascular pressure induced by many types of repetitive MSK activities. Skeletal muscle contraction and relaxation cycles during rhythmic physical activities cause regular oscillations in peripheral arterial and venous blood pressure or flow due to intermittent compression of the vasculature, while MSK movement can lead to periodic acceleration and deceleration of the intravascular volume of blood against gravity and inertia.

When rhythmic muscle contractions and MSK movements are favorably coordinated with the heart's pump cycle, the two pumping systems can augment one another, thereby increasing blood flow and perfusion to important areas of the body with less pumping energy expended by the heart. This favorable coordination of the two pumping systems can be referred to as "musculoskeletal counterpulsation" (MCP). During MCP, maximum rhythmic MSK-induced blood pumping consistently occurs while the heart is relaxing and refilling between contractions, and the maximum cardiac induced pumping consistently occurs between MSK maximal pumping events. On the other hand, when rhythmic muscle contractions and MSK movements occur with uncoordinated, or worse, unfavorably coordinated timing, blood flow and perfusion are decreased along with a concurrent decrease in pumping efficiencies. Unfavorable coordination occurs, for example, when the CV and MSK systems consistently pump blood maximally into the central circulation at substantially the same time during rhythmic physical activity. This unfavorable coordination of the two pumping systems can be referred to as "inverse musculoskeletal counterpulsation" (iMCP).

Typically, when individuals walk, run, bicycle, or participate in any rhythmic physical activity, most experience favorable coordination between MSK blood pumping and CV blood pumping only occasionally. Even when an individual's heart rate (HR) and exercise cadence happen to be equal, the respective timing of the two pumps may result in favorable or unfavorable coordination, or somewhere in between. Research has shown that a certain degree of "cardio-locomotor synchronization" can occur during rhythmic physical activity, in which the timing of an individual's MSK pump cycle relative to their heart's pump cycle tends, statistically, to naturally favor MCP. However, when such synchrony does occur, it is usually only a temporary phenomenon since HR and/or cadence can change as environmental factors vary (e.g., running in hilly terrain or variable wind), or with any of several physical changes, such as alterations in effort or speed, hydration, temperature, catecholamine levels or fatigue.

The benefits of favorable coordination between MSK movements and the heart's pump cycle can include improved perfusion and oxygenation of cardiac and peripheral skeletal muscle and possibly other tissues; a lower heart rate (HR) due to increased cardiac preload and stroke volume; a decrease in systolic blood pressure and pulse pressure; a decrease in required respiratory effort to meet the decreased oxygen demands; less muscle fatigue due to improved skeletal muscle perfusion. All of these benefits can combine to result in increased physiological efficiency, decreased myocardial stress, increased aerobic energy production capabilities and improved potential for aerobic fat metabolism, enhanced individual performance, and a potential increase in the health benefits and safety of rhythmic physical activity. Conversely, lack of coordination or unfavorable coordination between MSK movements and the heart's pump cycle can lead to the opposite of all of these effects.

As an individual's level of physical activity increases, the typical healthy heart increases its rate of pumping in response to the increased metabolic demands generated by the intensity of the action. In some hearts, this chronotropic capability is compromised and the individuals are said to be chronotropically incompetent. As a result, the individual faces symptoms that include shortness of breath during activities of modest intensity, which impairs quality-of-life. Individuals suffering from chronotropic incompetence are typically treated with an implanted rate-responsive pacemaker that stimulates the heart at a rate commensurate with the intensity of the activity. Pacemakers can use different mechanisms to determine rate responsiveness for a specific intensity of activity. Also, several mechanisms exist to measure the intensity of activity.

The earliest pacemakers were not rate responsive and had only the capability to provide stimulation pulses to the heart at a fixed cardiac pacing rate. A patient could feel wideawake when attempting to sleep or exhausted while attempting to exercise because their heart was beating at a steady rate that might be too high for comfortable resting but too low to meet the metabolic demands of many levels of physical activity.

To address problems with fixed-rate pacemakers, numerous methods have been used to adjust the pacing signals to the heart in response to the patient's immediate need. Such methods include accelerometry to sense the level of patient activity; thoracic impedance changes to reflect minute ventilation; temperature measurements as indicators of central venous temperature; QT sensors for measuring QT interval variations (a metric on the electrocardiogram/electromyogram). QT sensors are much better metabolic sensors and QT interval variations are a function of the intensity of activity and circulating catecholamine in the blood stream. Consequently, QT sensors are highly specific to exercise and post-exercise recovery as well as mental stress. Additionally, sensors capable of measuring physiologic responses, such as changes in blood pressure, blood oxygen content, pulse rate, blood flow, or myocardial or endocardial tissue acceleration, may also be used in conjunction with any of the above mentioned rate response sensors, to get more specific information about intra cardiac activity and to regulate the HR by appropriately timing the stimulating pulse from the pacemaker.

Each of these prior pacemaker rate-adjusting methods comes with their respective advantages and limitations. Nonetheless, adapting the pacing rate in response to one or more such sensing modalities offers advantages over the earlier non-rate responsive devices. None of these approaches however has attempted to coordinate the timing of the heart's pump cycle with the patient's repetitive physical activities.

Cardiac exercise stress testing is an important diagnostic modality that typically tests cardiac function during rhythmic physical activity (e.g. treadmill walking and running, and bicycle exercising). These tests are plagued by frequent false positive results. Uncontrolled rhythmic MSK activity that matches the patient's HR during the observation period may influence the apparent results, unbeknownst to the clinician performing the analysis.

BRIEF DESCRIPTION OF THE DRAWINGS

The specific features, aspects and advantages of the present invention will become better understood with regard to the following description and accompanying drawings where.

DETAILED DESCRIPTION

Figure 1:
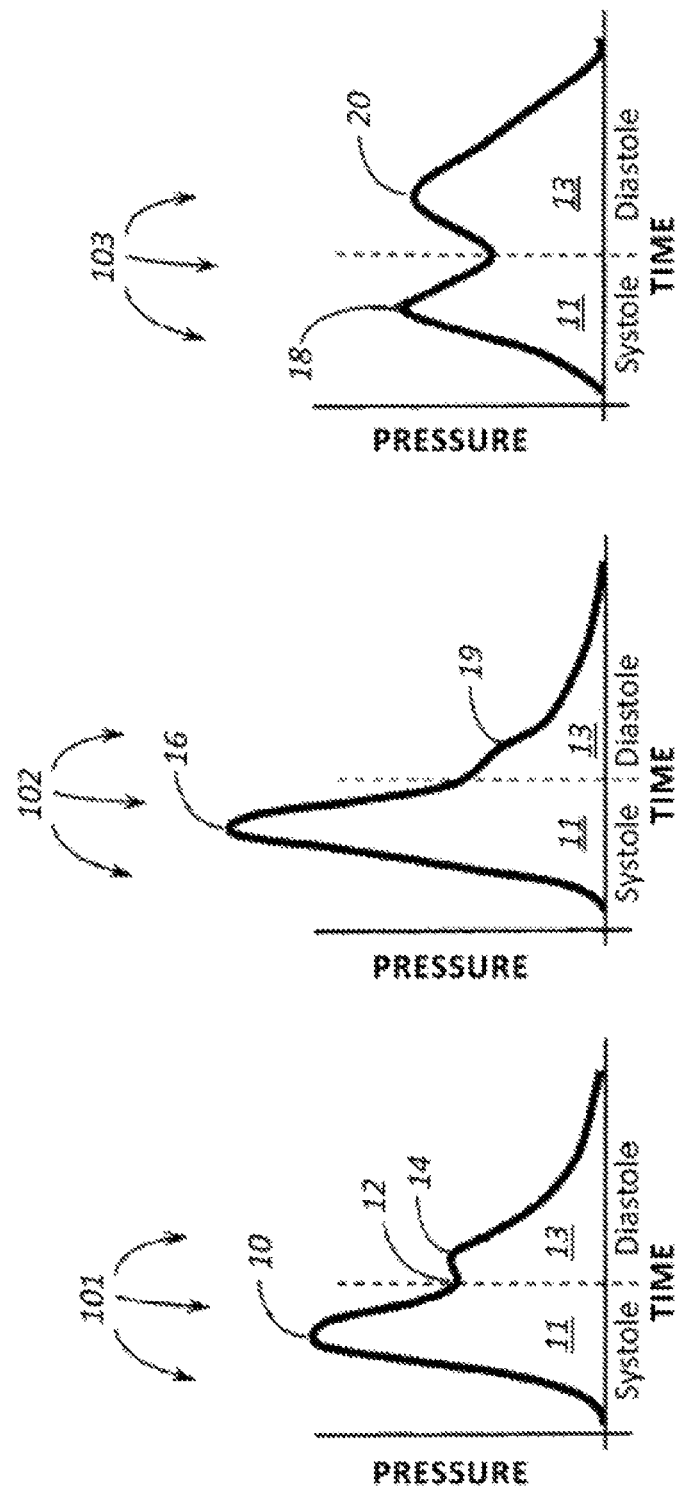
FIG. 1A illustrates a central arterial blood pressure curve for an individual at rest.
FIG. 1B illustrates a central arterial blood pressure curve for an individual during physical activity when musculoskeletal (MSK) movements and the heart's pump cycle are unfavorably coordinated.
FIG. 1C illustrates a central arterial blood pressure curve for an individual during physical activity when musculoskeletal (MSK) movements and the heart's pump cycle are favorably coordinated.

The present invention extends to methods, systems, apparatus, and computer program products for coordinating musculoskeletal and cardiovascular hemodynamics.

In general, embodiments of the present invention facilitate favorable coordination of musculoskeletal (MSK) pump timing and cardiac pump timing. Hemodynamic capacity and cardiac functional capabilities can be improved during rhythmic MSK activity by maintaining favorable coordination between the timing of blood pumped by the rhythmic MSK activity and the timing of a corresponding cardiac pumping cycle. In some embodiments, favorable coordination includes an individual's artificial pacemaker providing electrical signals to cause the heart to contract in proper synchrony with the individual's sensed repetitive MSK activity. In other embodiments, favorable coordination includes an individual voluntarily pumping blood via MSK movement or skeletal muscle contraction in proper synchrony with the individual's sensed heart pump timing. Real-time measurements of an individual's heart pump timing and rhythmic MSK activity timings (e.g., movement or MSK contraction timing) can be used to provide biofeedback or control enabling an individual to maintain musculoskeletal counterpulsation (MCP) during rhythmic physical activity for extended amounts of time.

In "beat to the step" embodiments, MCP is implemented in an automated fashion using an artificial cardiac pacemaker. A pacemaker can sense both cardiovascular (CV) and physical activity for an individual. For example, a pacemaker can include movement sensors (e.g. pacemaker accelerometers or other sensors) that sense an individual's rhythmic physical movements, such as regular movements that occur with ambulation or many forms of exercise. Based on the sensed movement, the pacemaker can adjust the timing of any paced cardiac cycles such that the CV pump cycle is coordinated with MSK pump cycles so that left ventricular ejection occurs at a timing in-between MSK activity-induced blood pumping events (e.g., foot strikes during ambulation). As such, maximal MSK activity-induced blood pumping occurs during the targeted portion of cardiac diastole (this can be referred to as pacemaker-induced counterpulsation). Pacemaker-induced counterpulsation (PC) benefits an individual's hemodynamics, including potentially increasing tissue perfusion, while also decreasing systemic vascular resistance, arterial pulse pressure, and the metabolic requirements of the heart.

A cardiac-MSK coordinated pump system can be calibrated to optimally coordinate the relaxation phase of the cardiac pumping cycle to the timing of maximal MSK activity-induced blood flow.

In other "step to the beat" embodiments, an individual can be prompted to adjust the timing of MSK activity for coordination with the CV pump cycle so that left ventricular ejection occurs at a timing in-between rhythmic MSK events (e.g., foot strikes during ambulation, pedal pushes during bicycling, or isometric muscular contractions during upper extremity exercise). In "step to the beat" embodiments, individuals can be provided with additional guidance (i.e., beyond MSK pump timing), for example, in helping the individual to coordinate breath timing with MSK activity ("breathe to the step" or "breathe to the beat"), while simultaneously achieving MCP. For example, individuals can be provided with guidance to breathe at a cadence matching a multiple of their steps.

A graphical user interface (GUI) can provide an individual with visual feedback on the accuracy of achieving MCP. The visual feedback can relate to the coordination of MSK activity and CV pump cycle. The GUI can show a cadence graphic along with a HR graphic on the same graphical scale. As the individual gets closer to matching MSK activity timing and CV pump cycle timing, the cadence graphic and the HR graphic move closer to one another. When MSK activity timing and CV pump cycle timing are appropriately matched, the cadence graphic and the HR graphic are on top of one another. As the individual gets further from matching MSK activity timing and CV pump cycle timing, the cadence graphic and the HR graphic move away from to one another.

Other types of GUIs can be integrated into video games, such as, for example, "Dance Dance Revolution". An individual can score points for a target physical action when the timing of the target physical action (e.g., an MSK pump) is in proper sync with the target timing of the beat (pump) of the individual's heart.

Individuals (e.g., athletes) can be weaned from devices that assist with favorable coordination of MSK pump timing and cardiac pump timing. Algorithms can be used to help individuals feel and recognize the effect of improved blood flow dynamics without assistance from external devices.

In other embodiments, the timing of rhythmic physical activity relative to a monitored Electrocardiogram (ECG) is analyzed during an exercise stress test. The analysis can expose ECG changes potentially (or likely) to be related to effects of inverse musculoskeletal counterpulsation (iMCP), as opposed to some other cardiac condition such as heart disease, on cardiac stress or perfusion. The analysis can also identify ECG changes that can appear to reflect pathology (e.g. apparent ST segment depression) but also can be readily caused by motion artifacts that can occur when inertial changes during rhythmic step timing are consistently aligned with portions or aspects of the heart's cycle (and that might otherwise be indicated as a false positive for a cardiac condition, such as, coronary artery disease.)

In general, embodiments of the invention also enable a user to avoid (possibly inadvertent) unfavorable coordination of MSK movement and skeletal muscle contraction cycles with cardiac pumping cycle during physical activity.

In the following description of the present invention, reference is made to the accompanying drawings, which form a part hereof, and in which is shown by way of illustration specific embodiments in which the invention is may be practiced. It is understood that other embodiments may be utilized and structural changes may be made without departing from the scope of the present invention.

Embodiments of the present invention may comprise or utilize a special purpose or general-purpose computer including computer hardware, such as, for example, one or more processors and system memory, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, embodiments of the invention can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM). Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered Storage, such as FusionIO). Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics (including wearable electronics, such as, wristbands and ear pieces), pacemakers, fitness equipment (e.g., treadmills) network PCs, game consoles, minicomputers, mainframe computers, mobile telephones, PDAs, tablets, pagers, routers, switches, various storage devices, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Embodiments of the invention can also be implemented in cloud computing environments. In this description and the following claims, "cloud computing" is defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service (SaaS), Platform as a Service (PaaS), Infrastructure as a Service (IaaS), and deployment models (e.g., private cloud, community cloud, public cloud, hybrid cloud, etc.). Databases and servers described with respect to the present invention can be included in a cloud model.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

For the purpose of clarity, the following terminology and abbreviations are used throughout this description and following claims:
CC Cardiac Cycle, equivalently Cardiovascular Cycle
CV Cardiovascular
ECG Electrocardiogram
ECP External Counterpulsation
EMG Electromyogram
HR Heart Rate
iMCP Inverse Musculoskeletal Counterpulsation
MCP Musculoskeletal Counterpulsation
MSK Musculoskeletal
PC Pacemaker-Induced Counterpulsation
RRI R-wave to R-wave interval (R-R time interval) within an ECG signal In this application, "MSK activity" and "MSK pumping" includes at least one of muscle contraction and MSK movement and their related inertial and pumping effects on blood pressure and blood flow. In addition, the terms "cardiac pumping" and "cardiovascular pumping" are used interchangeably.

In general, hemodynamic effects of musculoskeletal counterpulsation (MCP) can be illustrated by comparing an example central arterial blood pressure curve of an individual at rest to example central arterial blood pressure curves of the same individual during physical activity. FIG. 1A depicts a graph 101 of a central arterial blood pressure curve for a typical healthy young elastic aorta when the individual is at rest. Graph 101 depicts systolic pressure wave 10 during cardiac systole 11. Systolic pressure wave 10 ends and diastolic pressure wave 14 begins at aortic valve closure (dicrotic notch 12). Graph 101 depicts diastolic pressure wave 14 during cardiac diastole 13.

FIG. 1B depicts a graph 102 of an example of a central arterial blood pressure curve in the same individual during physical activity when MSK movements and the heart's pump cycle are unfavorably coordinated, as occurs with iMCP. That is, when maximal pumping of blood towards the heart by the MSK system occurs at the same time as cardiac systole 11 (heart pumping blood to into the aorta). This unfavorable condition causes the cardiac and MSK pumping mechanisms to temporarily directly oppose the action of one another, as the two pumps simultaneously push blood in opposite directions, towards one another, within the same central arteries. This can lead to multiple undesirable effects, including any or all of: decreased pumping efficiency, increased systolic blood pressure (e.g., as indicated by systolic pressure wave 16), increased HR, increased myocardial energy demand, decreased arterial perfusion, decreased muscle perfusion, and earlier fatigue. Each of these undesirable effects can lead to increases in health risk, particularly in extreme or at risk circumstances, due to the possibility of inadequate myocardial perfusion concurrent with an increased myocardial work load. The detrimental effect can be made worse when the unfavorably coordinated pumping results in lower central arterial and venous pressure during diastole (e.g., as indicated by diastolic pressure wave 19), potentially decreasing both myocardial perfusion and filling of the hearts pumping chambers.

Conversely, FIG. 1C depicts a graph 103 of an example of a central arterial blood pressure curve in the same individual during physical activity when MSK movements and the heart's pump cycle are favorably coordinated, as occurs with MCP. That is, when maximal relaxation of the MSK system is during cardiac systole 11 and when maximal pumping of blood towards the heart by the MSK system is during cardiac diastole 11 (i.e., the heart at rest refilling with blood). Maximal relaxation of the MSK system during cardiac systole 11 decreases systolic central blood pressure (e.g., as indicated by systolic pressure wave 18). On the other hand, maximal pumping of blood towards the heart by the MSK system during cardiac diastole 13 increases diastolic central blood pressure (e.g., as indicated by diastolic pressure wave 20).

As individuals age, the aorta loses its elasticity, leading to a classic increase in baseline systolic blood pressure, since the heart is pumping blood into a stiffer tube (aorta). Loss of aortic elasticity also leads to a decrease in diastolic blood pressure, because the stiff aorta is less able to maintain pressure without the heart actively generating pressure, as it does during systole. Thus, graph 102 can also represent characteristics of a central arterial (e.g., aortic) waveform that one might expect to see in an elderly individual at rest and is contrary to a healthy young individual at rest, as depicted in graph 101.

Figure 2:
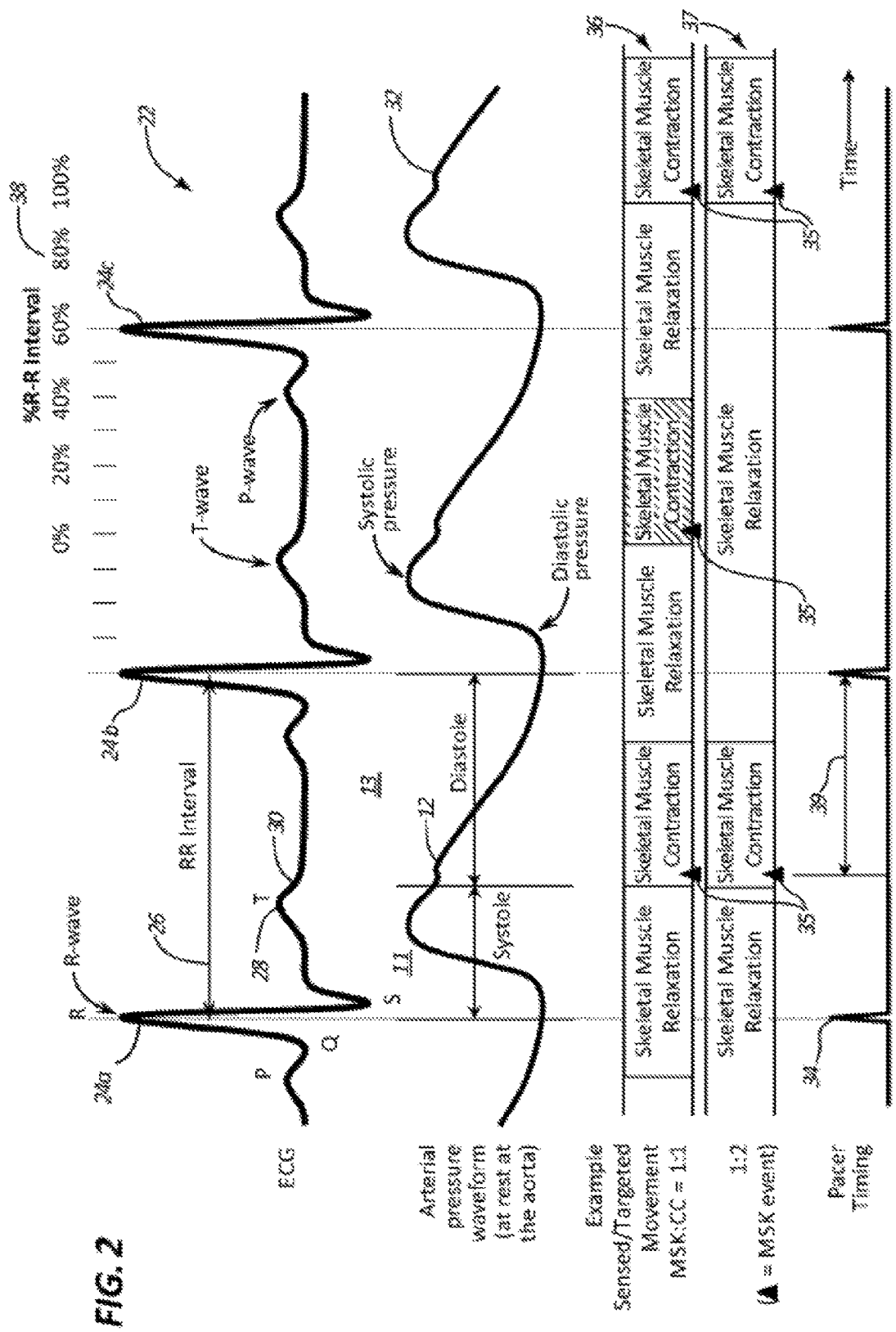
FIG. 2 illustrates example timing relationships between an ECO tracing, a central arterial pressure waveform, and skeletal muscle contraction cycles relative to the timing of an example cardiac pacing signal for an individual.

FIG. 2 illustrates example timing relationships between an ECG tracing 22, central arterial pressure waveform 32, skeletal muscle contraction cycles 36 and 37, and the timing of an example cardiac pacing signal 34 for an individual. ECG tracing 22 depicts various different waves including P-waves, Q-waves, R-waves, S-waves, and T-waves.

R-waves 24 (including 24a, 24b, and 24c) represent depolarization of the myocardium of the ventricular walls of the heart. R-waves 24 can be utilized in the measurement of HR via the measurement of the duration of R-to-R intervals (RRI) 26. RRIs 26 can vary beat-to-beat and measurement of that variation is called heart rate variability (HRV). T-wave portion 28 reflects ventricular repolarization. T-wave end 30 can be used as a marker of the approximate timing of aortic valve closure during the heart's pumping cycle. T-wave end 30 and aortic valve closure also both occur with timing that corresponds to dicrotic notch 12 of a central arterial pressure wave.

Examples of targeted MSK timing 36 and 37 both include brief periods of skeletal muscle contraction during cardiac diastole 13 followed by periods of relaxation. MSK events 35 identify a period in time that corresponds to, for example, the onset of activity-related muscle contractions. In targeted MSK timing 36, the muscle contractions are timed by the user to begin at prompts corresponding to MSK events 35 that repeat, in this example, with each instance of the Cardiac Cycle (CC). That is MSK:CC=1:1. In targeted MSK timing 37, the prompts and muscle contractions repeat with every other CC. That is MSK:CC=1:2. The user can opt or be directed to initiate an MSK event with each prompt, or multiple times per prompt (e.g. prompt corresponds to every other foot strike during running).

As depicted, pacer timing signal 34 (e.g., for timing a corresponding pacemaker) includes delay time 39. Delay time 39 indicates the equivalent MSK event 35-to-R-wave 24 relationship for initiating the depolarization of the ventricles artificially to favorably coordinate MSK and heart pumps. (Pacer timing signal 34, in this example, may correspond most closely to Ventricular Pacing; alterative pacing signal characteristics are also contemplated (e.g., Atrial, AV synchronous, and Biventricular Pacing), each of which would require a different delay time 39 to achieve the equivalent MSK event 35 to cardiac muscle contraction timing relationship.)

Scale 38 represented the percent of the RRI 26 nomenclature used herein. For example, 0% and 100% represent events timed coincident with the R-waves 24, while 25% of the RRI is a quarter of the way between successive R-waves 24 (e.g., between 24b and 24c), and 50% is the mid-point between R-waves 24. Scale 38 can alternatively be expressed fractionally as a value from zero to one, in units of degrees between zero and 360 degrees, or in radians between zero and $2\pi$ radians (e.g., 25%=0.25=90 degrees=1.57 radians), equivalent to the percentage terminology. Values greater than 100% describe events in a subsequent R-R interval (e.g., 130% represents a 30% location in the following interval).

Coordinating CV Pumping with MSK Pumping Through Electronic Cardiac Pacing

In this description and the following claims, the terms pacemaker, artificial pacemaker, electronic pacemaker and extrinsic pacemaker are used interchangeably to describe artificial heart pacing devices commonly provided in a patient whose heart's natural intrinsic pacemakers are not functioning properly, or when cardiac resynchronization therapy can otherwise potentially improve quality of life in the face of impaired cardiac function.

Embodiments of the invention enable an artificial pacemaker, or other implantable system, such as a single chamber, dual chamber, or biventricular pacemaker supporting a patient with a heart conditions (e.g., symptomatic bradycardia, chronotropic incompetence, heart block, congestive heart failure, etc.) to operate in favorable synchrony with a sensed rhythmic MSK activity in a patient. Favorable synchrony includes the relaxation phase of the cardiac pumping cycle (diastole) and the timing of maximal central blood pumping via MSK movement and skeletal muscle contraction (e.g. foot strike while walking) substantially aligning. Favorable synchrony also includes the contraction phase of the cardiac pumping cycle (systole) and the timing of maximal skeletal muscle relaxation substantially aligning, thereby optimizing muscle perfusion and blood pressures during those activities. Numerous patients requiring cardiac rhythm management have severely compromised cardiac function and any modest increase in cardiac perfusion can significantly increase cardiac contractility leading to better hemodynamics for the patient.

In general, a cardiac-MSK coordination system can determine a target heart pump timing using single or multiple sensors responsive to patient activity, and then use this timing information when creating heart-pacing signals.

Figure 3A:
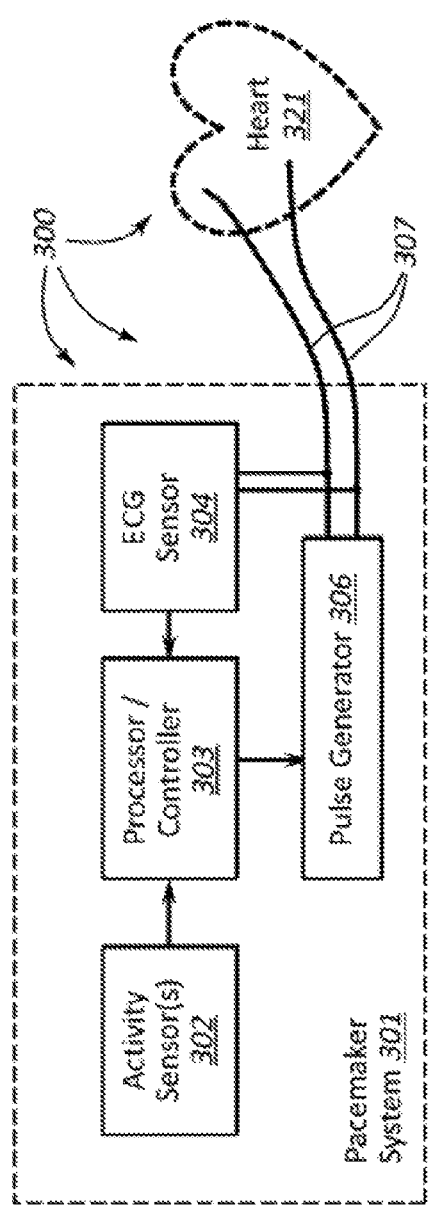
FIG. 3A illustrates an example architecture for a pacemaker system.

FIG. 3A illustrates an example architecture 300 for implantable pacemaker system 301. As depicted, implantable pacemaker system 301 includes activity sensor(s) 302, processor (or other controller) 303, ECG sensor 304, pulse generator 306, one or more electrical lead(s) 307. Electrical lead(s) 307 connect implantable pacemaker system 301 to heart 321. Lead(s) 307 can be of any standard length including, for example, very short prongs that comprises the leads of what are referred to as "leadless pacemakers". All or a portion of pacemaker system 301 can be implanted in individual 322 to assist with pumping individual 322's heart 321. Embodiments of this system 301 can include an implantable cardio-defibrillator (ICD) along with the pacemaker. Implantable pacemaker system 301 can also include other affiliated components (not shown), such as, for example, additional physiological sensor(s), a battery, etc.

Activity sensor(s) 302 can be built into pacemaker system 301 (or a defibrillator). Activity sensor(s) 302 can include one or more of a variety of different components including but not limited to: uniaxial and multiaxial accelerometers, magnetometers, gyroscopes, piezoelectric materials, pressure sensors, and other motion/activity sensors that are responsive to MSK activity in an individual. Accelerometers can be 3-axis sensors and can be packaged with gyroscopes, magnetometers, temperature monitors and other sensors. As such, embodiments including accelerometers may inherently include any of these other type of sensors. Further, any combination of commonly used and available internal or external activity sensors that are capable of reliably measuring rhythmic MSK activity can provide the activity sensing function of the pacemaker device, thereby enabling PC through the favorable coordination of MSK pump timing and cardiac pump timing.

Activity sensor(s) 302 can be co-located within implantable pacemaker system 301 or within a lead or otherwise integrated form factors in line with implantable pacemaker system 301. Generally, activity sensor(s) 302 sense(s) and interpret(s) sensor signals in order to detect and characterize movement and its timing during rhythmic physical activities, including but not limited to walking, running, swimming, climbing, rowing, etc. Signals from activity sensor(s) 302 can be sent to processor 303. Alternatively, the processing for detecting, characterizing movement and its timing from activity sensor(s) 302 signals may be performed by processor 303 without departing from the concepts described herein.

ECG sensor 304 is configured to monitor and interpret electrical activity of heart 321 over a period of time as detected via leads 307 (e.g., as represented by EGC signal 22 in FIG. 2). ECG sensor 304 with leads(s) 307 (or other conduction technology) can be used to sense natural depolarization of the heart, minute ventilation via impedance, and contractility of myocardium using bipolar leads. Signals (indicating these and other types of measurements) from ECG sensor 304 can be sent to processor 303. In some embodiments, a baseline (lower frequency) component of an ECG signal is sensed and used to determine repetitive movement. In further embodiments, pacemaker system 301 can include or be integrated with additional internal physiological sensors (not shown), for example, sensors that measure arterial or cardiac pressures, pH, glucose, lactate, cardiac enzymes, or blood gas concentrations.

The available real-time physiological measurements can be used in algorithms to measure and control optimal hemodynamics. For example, an automated calibration algorithm can be programmed to enable the system to determine the optimal relative timing for CV pump vs. MSK pump by pacing the heart such that ventricular contraction is systematically triggered at different timing locations during a rhythmic MSK pumping cycle, while the individual's physiological response is measured via physiological sensors. Measures that change in correlation with relative CV vs. MSK pump timing, for example fluctuations in contractility, blood pressure, cardiac output, tissue oxygenation, tissue pH and minute volume, can then be used to identify optimal target CV pump vs. MSK pump timings.

Processor 303 is configured with signal processing capabilities. Processor 303 can receive signals from activity sensor(s) 302 and/or ECG sensor 304. The signal processing capabilities can process received signals to identity refined motion elements, such as, impact and orientation from ground reaction forces (e.g., heel strike, loading response, etc.) and derive metrics, such as, stride frequency (cadence), maximal muscle contraction timing, timing or magnitude of rhythmic changes in inertia, precise step timing, changes in elevation, duration of foot-ground contact time, foot strike ergonomics, balance, etc. Based on identified refined motion elements and/or derived metrics, processor 303 can interoperate with pulse generator 306 to control the timing of stimulating heart 321 (e.g., to favorably coordinate CV pump timing with detected MSK pump timing).

Pulse generator 306 and lead(s) 307 are configured to process information and electrically stimulate cardiac myocytes above a depolarization threshold. Electrical stimulation above the depolarization threshold activates the conduction system of the heart and causes cardiac systole. Placement of lead(s) 307 (e.g. right atrium, one or both ventricles) depends on the pacemaker functionality desired (e.g. atrial, ventricular, AV synchronized, or biventricular pacing).

Pulse generator 306 (or other additional pacemaker system components) can also include built-in rate-responsive pacing circuitry that generates stimulation pulses on demand at a rate and timing determined at least in part by the frequency and timing of the repetitive MSK activity. Target timing of the stimulation pulses during certain rhythmic physical activities can be determined by computing a timing value based on a function of the sensed MSK pump timing.

Implantable pacemaker systems are not limited to internal activity sensors. Implantable pacemaker systems can utilize other (external) independent physiologic sensors or a combination of physiologic sensors, such as, for example, respiratory, cardiac function, motion, force, temperature, EMG, ECG, electroencephalogram, photoplethysmogram, or other sensors responsive to body motions. These other sensors can further characterize drivers of MSK pumping, including the force of skeletal muscle contraction and relaxation, and inertial changes that occur with body movement as well as to reveal the impact of MSK pump timing on other organ systems.

Figure 3B:
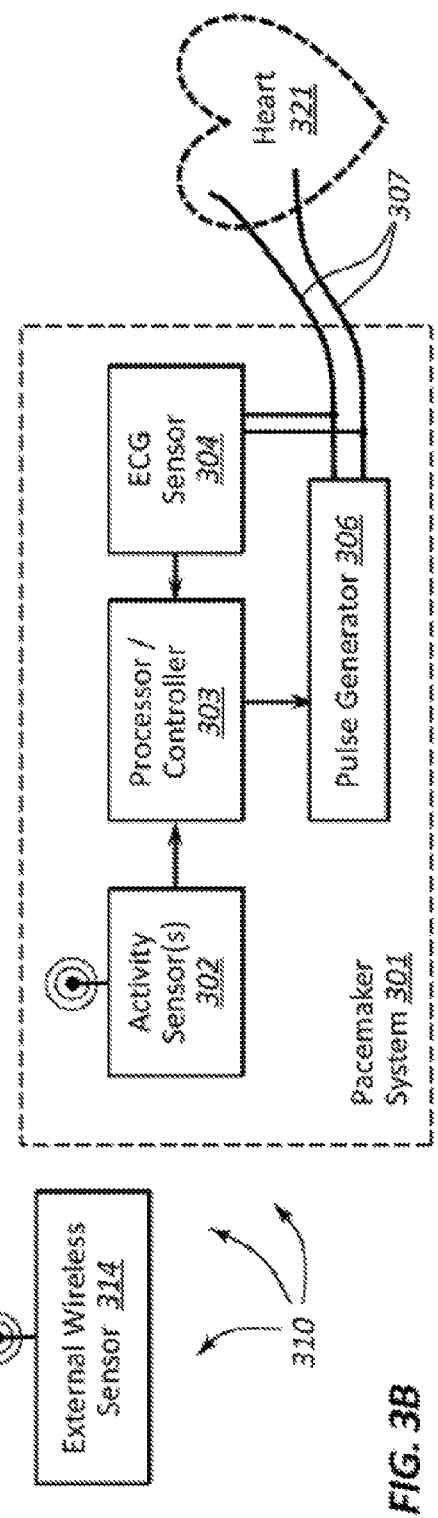
FIG. 3B illustrates an example architecture for a pacemaker system.

For example, FIG. 3B illustrates an example architecture 310 for implantable pacemaker system 311. As depicted, implantable pacemaker system 311 includes receiver 313, processor (or other controller) 303, ECG sensor 304, pulse generator 306, and electrical lead(s) 307. Electrical lead(s) 307 connect implantable pacemaker system 311 to heart 321. Pacemaker system 311 can be implanted in individual 322 to assist with pumping individual 322's heart 321.

Also depicted are external wireless sensor(s) 312. External wireless sensor(s) 312 is external to (e.g., not implanted inside of) an individual. External wireless sensor(s) 312 can include one or more of any of the described MSK activity sensors and one or more of the other described implanted or external physiological measurement sensors. External wireless sensor(s) 312 can also include wireless communication capabilities for communicating with receiver 313. Similarly, receiver 313 can include wireless communication capabilities for communicating with external wireless sensor(s) 312.

Generally, external wireless sensor(s) 312 sense(s) and interpret(s) sensor signals in order to detect and characterize movement and its time during rhythmic physical activities, including but not limited to walking, running, swimming, climbing, rowing, etc., or the physiological effect of rhythmic MSK activity timing relative to CV pump timing. Signals from external wireless sensor(s) 312 can be sent via wireless communication to receiver 313. Receiver 313 can receive signals via wireless communication from external wireless sensor(s) 312. Receiver 313 can forward signals from external wireless sensor(s) 312 to processor 303. Processing of signals from external wireless sensor(s) 312 to derive relevant information (such as MSK event timing 35) can be accomplished within an external wireless sensor 312, or within processor/controller 303, without departing from the concepts described herein.

The other components of pacemaker system 311 operate similarly to like numbered components of pacemaker system 301.

As such, an activity sensor can be an externally worn device or an implanted (and possibly pacemaker integrated) device that communicates via wired or wireless transmission with processor 303 and pulse generator 306. In some embodiments, a pacemaker system includes both implanted sensor(s) (e.g., activity sensor(s) 302, other physiological sensors) and external sensors (e.g., external wireless sensor(s) 312) and receiving mechanisms (e.g., receiver 313). In these embodiments, processor 303 and pulse generator can receive and process signals from both internal and external sensors.

Accordingly, utilizing the described (and other) components, a pacemaker system can facilitate measurement of MSK activity and depolarize the heart at the proper time to optimize hemodynamics. Similar functionality can be merged with conventional pacing applications used for therapeutic purposes (e.g., treating arrhythmia, bradycardia, chronotropic incompetence, etc.) by adjusting the specific timing of those pacing signals to properly coordinate the heart pump timing with the sensed MSK activity; or, if more generally indicated, by coordinated timed pacing of the heart with the MSK events whenever persistent rhythmic movement is detected and, for example, HR and cadence are sufficiently similar and/or meet specified conditions.

Figure 4:
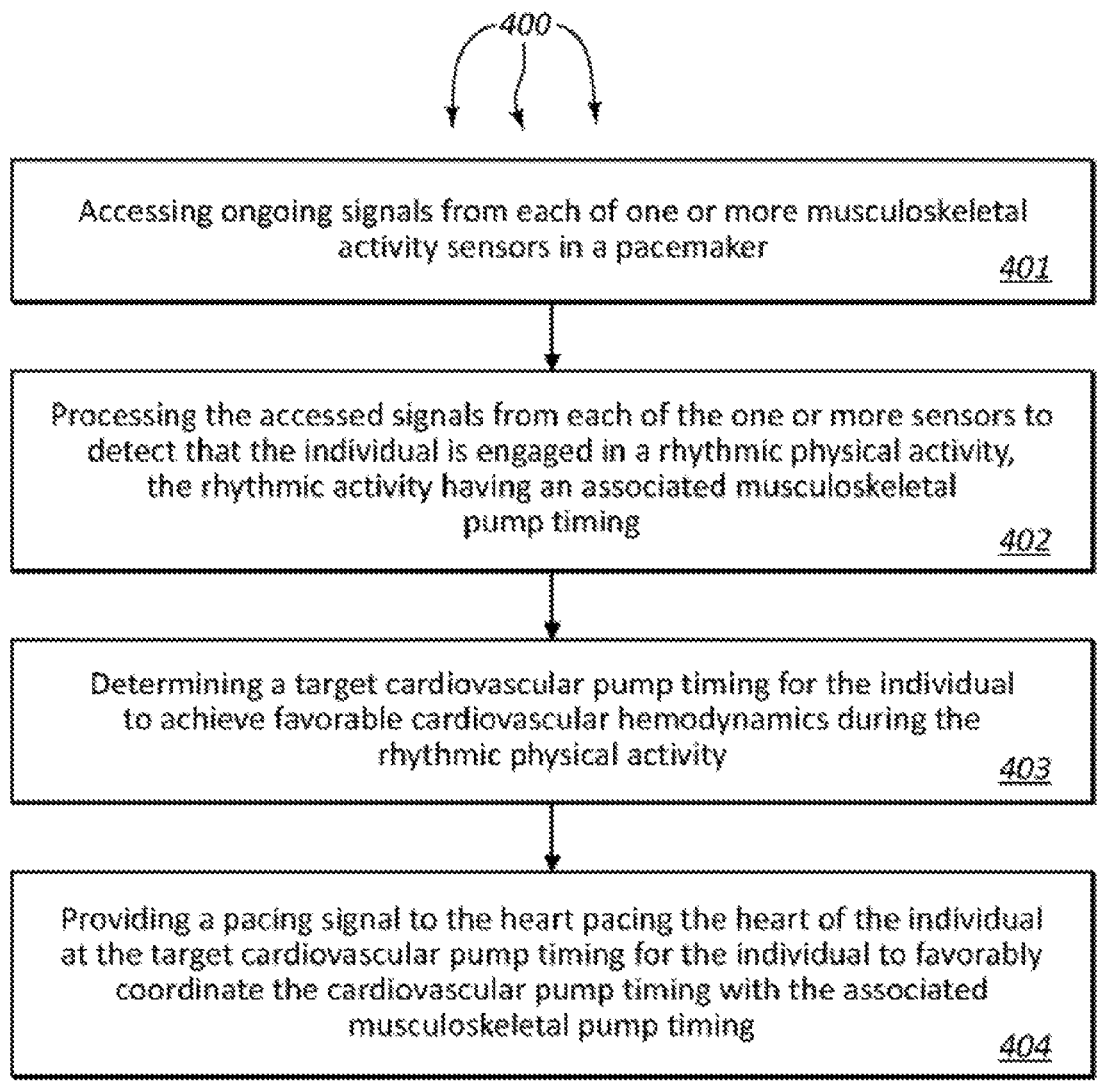
FIG. 4 illustrates a flow chart of an example method for coordinating cardiovascular pump timing with detected musculoskeletal pump timing to facilitate favorable cardiovascular hemodynamics in an individual.

FIG. 4 illustrates a flow chart of an example method 400 for coordinating cardiovascular pump timing with detected musculoskeletal pump timing to facilitate favorable cardiovascular hemodynamics in an individual. Method 400 will be described with respect to the components of architectures 300 and 310.

Method 400 includes accessing ongoing signals from each of one or more musculoskeletal activity sensors in a pacemaker (401). For example, processor 303 can access a signal from one or more sensors in activity sensor(s) 302 and/or from one or more sensors in external wireless sensor(s) 312 and/or from ECG sensor 304.

Method 400 includes processing the accessed signals from each of the one or more sensors to detect that the individual is engaged in a rhythmic physical activity, the rhythmic activity having an associated musculoskeletal pump timing (402). For example, processor 303 can process an accessed signal from one or more sensors in activity sensor(s) 302 and/or from one or more sensors in external wireless sensor(s) 312 and/or from ECG sensor 304 to determine that individual 322 (which pacemaker system 301 or 311 can be implanted in) is engaged in rhythmic physical activity. The rhythmic physical activity individual 322 is engaged in can have an associated MSK pump timing.

Method 400 includes determining a target cardiovascular pump timing for the individual to achieve favorable cardiovascular hemodynamics during the rhythmic physical activity (403). For example, processor 303 can determine an adjustment to CV pump timing for heart 321 to favorably coordinate the CV pump timing of heart 321 with the MSK pump timing associated with the rhythmic physical activity individual 322 is engaged in.

Method 400 includes providing a pacing signal to the heart pacing the heart of the individual at the target cardiovascular pump timing for the individual to favorably coordinate the cardiovascular pump timing with the associated musculoskeletal pump timing (404). For example, pulse generator 106 can implement the determined adjustment to CV pump timing for heart 321 to facilitate counterpulsation within individual 322 while individual 322 is engaged in the rhythmic physical activity. That is, pulse generator 106 can implement an adjustment to CV pump timing for heart 321 to facilitate a central arterial blood pressure curve for individual 322 that is similar to that of FIG. 1C.

Figure 5:
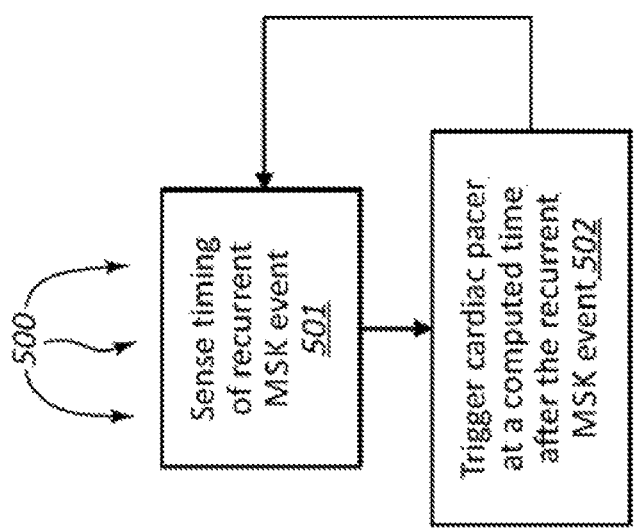
FIG. 5 illustrates a flow chart of an example method for coordinating timing of cardiac pacing to optimize hemodynamics through musculoskeletal (MSK) counterpulsation.

Other mechanisms for improving hemodynamics within an individual are also contemplated. Some mechanisms calculate rhythmic MSK events and cadence using one or more activity sensors and then electrically stimulate the contraction of the heart to occur at a target timing relative to the previous or next anticipated MSK event. For example, FIG. 5 illustrates a flow chart of an example method 500 for coordinating timing of cardiac pacing to optimize hemodynamics through MSK counterpulsation. Method 500 will be described with respect to the components of architectures 300 and 310.

Method 500 includes sensing the timing of a recurrent MSK event (501). For example, one or more sensors in activity sensor(s) 302 and/or one or more sensors in external wireless sensors(s) 312 can interoperate with processor 303 to sense the timing of a rhythmic MSK event for individual 322. Method 500 includes triggering a cardiac pacer at a computed time after the recurrent musculoskeletal event (502). For example, processor 303 and pulse generator 306 can interoperate to trigger depolarization of heart 321 at a computed time after the regularly recurring MSK event for individual 322.

Algorithms and sensors can be utilized to identify instances when pacing the heart at a rate that approximates the cadence of the rhythmic physical activity would be appropriate for the level of exertion. In those instances, an electrical pacing system utilizes further timing algorithms and signals from MSK activity sensors to identify the timing when a pacemaker's electrical stimulation results in left ventricular depolarization timing that is coordinated to the MSK activity cycle timing such that MCP is optimized (i.e., PC).

Figure 6:
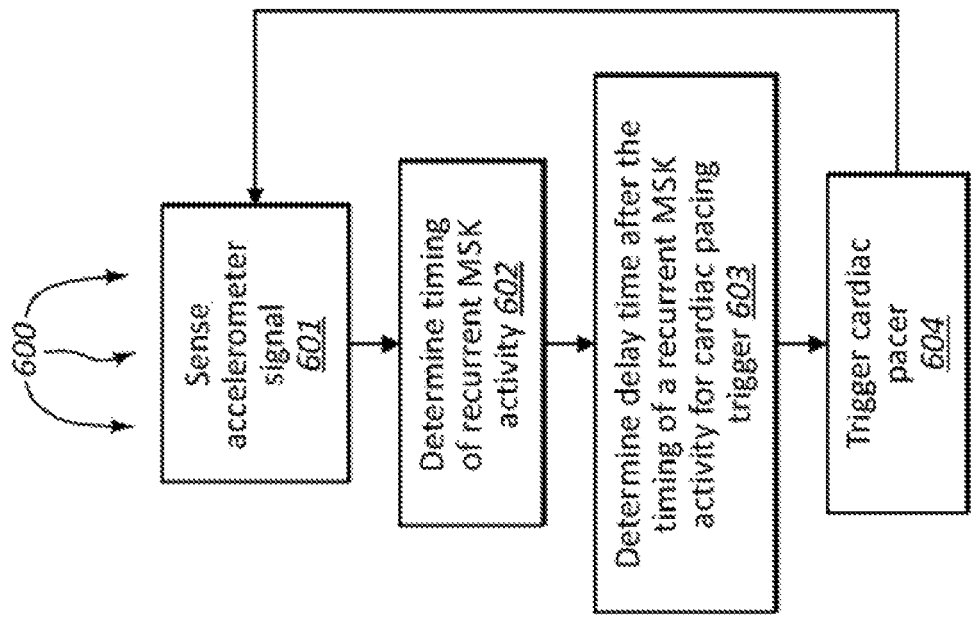
FIG. 6 illustrates a flow chart of an example method for coordinating timing of cardiac pacing to optimize hemodynamics through musculoskeletal (MSK) counterpulsation.

In some embodiments, an accelerometer is used to detect MSK activity. Additional embodiments include accelerometers along with other movement sensors, for example, gyroscopes and magnetometers, which are frequently packaged together and can add further resolution to movement sensing. FIG. 6 illustrates a flow chart of an example method 600 for coordinating timing of cardiac pacing to optimize hemodynamics through MSK counterpulsation. Method 600 will be described with respect to the components of architectures 300 and 310.

Method 600 includes sensing an accelerometer signal (601). For example, processor 303 can sense an accelerometer signal from an accelerometer in one of activity sensor(s)

302 or external wireless sensor(s) 312. Method 600 includes determining the timing of a recurrent MSK activity from the sensed accelerometer signal (602). For example, processor 303 can determine the timing (e.g., corresponding, for example, to MSK event 35) of a recurrent MSK activity for individual 322 from the signal sensed from the accelerometer in one of activity sensor(s) 302 or in external wireless sensor(s) 312.

Method 600 includes determining a delay time (e.g., delay 39) after the timing of a recurrent MSK activity for cardiac pacer trigger (603). For example, processor 303 can determine a delay time after the timing of the recurrent MSK activity for individual 322 for triggering heart 321. Method 600 includes triggering the cardiac pacer at the determined delay time (604). For example, processor 303 and pulse generator 306 can interoperate to trigger a pulse to heart 321 at the determined delay time after the timing of the recurrent MSK event for individual 322.

In some embodiments, a heart can be electrically stimulated so as to initiate a cardiac contraction at a precise phase or timing location within a MSK cycle or a time delay relative to a recurrent MSK cycle event. The cardiac electrical stimulation trigger may be based on a percent of the step-to step-interval; a fixed time delay relative to an identified recurrent event in the MSK cycle; or a calculated timing based on at least one of physiologic, historical, test results (e.g., calibration based) and demographic data after the MSK event or prior to a predicted next MSK event. The timing can be optimized such that the cardiac cycle reaches diastole just as the next predicted MSK pumping event occurs. For MSK activity that repeats with a generally stable rhythm or period, the electrical stimulation can be similarly induced according to the same rate and rhythm, phase shifted properly to achieve the hemodynamic effects of PC.

Such properly synchronized behaviors may create some of the hemodynamic effects and benefits seen with external counterpulsation (ECP) and intra-aortic balloon pump (IABP) devices. Furthermore, as with ECP and IABPs, favorable episodes of counterpulsation may occur when the cardiac rate is an integer multiple of the rhythmic MSK activity rate (i.e., HR:MSK rate=1:1, 2:1, 3:1, 4:1, etc.), as the timing relationship remains approximately constant relative to the particular marker of the CCs in which the MSK activity occurs, or vice versa.

Figure 7:
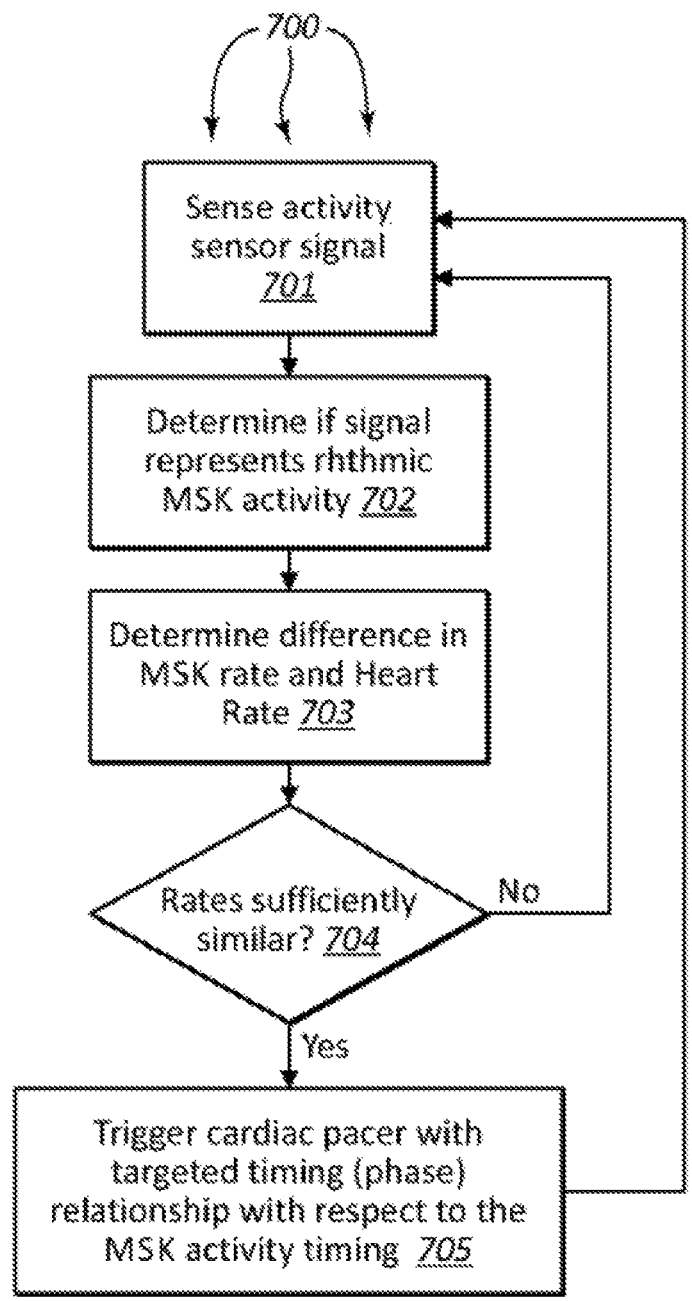
FIG. 7 illustrates a flow chart of an example method for coordinating timing of cardiac pacing to optimize hemodynamics through pacemaker-induced counterpulsation (PC).

FIG. 7 illustrates a flow chart of an example method 700 for coordinating timing of cardiac pacing to optimize hemodynamics through PC. Method 700 will be described with respect to the components of architectures 300 and 310.

Method 700 includes sensing an activity sensor signal (701). For example, processor 303 can sense an accelerometer signal from an accelerometer in one of activity sensor(s) 302 or external wireless sensor(s) 312. Method 700 includes determining if the activity sensor signal represents rhythmic activity (702). For example, processor 303 can determine if the accelerometer signal from the accelerometer in one of activity sensor(s) 302 or external wireless sensor(s) 312 represents that individual 322 is engaged in rhythmic MSK activity, for example, ambulation.

Method 700 includes determining continuously or intermittently the difference between the MSK activity rate and the HR (703). For example, processor 303 can determine the difference between a rhythmic MSK activity rate that individual 322 is performing and the HR (or the target HR range appropriate for the sensed rhythmic physical activity) of heart 321. Method 700 includes determining if the activity rate and the HR (or the target HR range appropriate for the sensed rhythmic MSK activity) is sufficiently similar (decision block 704). For example, processor 303 can determine if the activity rate of individual 322 and the HR (or the target HR range appropriate for the sensed rhythmic physical activity) of heart 321 are sufficiently similar. If the activity rate and HR (or the target HR range appropriate for the sensed rhythmic physical activity) are not sufficiently similar (NO at 704), method 700 returns to 701. If the activity rate and HR (or the target HR range appropriate for the sensed rhythmic physical activity) are sufficiently similar (YES at 704), method 700 proceeds to 705.

Method 700 includes triggering a cardiac pacer with a targeting time (or equivalently, phase) relationship with respect to MSK activity timing (705). For example, processor 303 and pulse generator 306 can interoperate to trigger pulses to heart 321 at targeted times based on the timing of MSK activity for individual 322.

A variety of different triggers can be used to initiate PC, including but not limited to, increased metabolic demands as identified by minute ventilation and/or the activity sensor, a sensed cyclical MSK activity rhythm detected by the activity sensor, pre-programmed activation during certain times of the day, or triggered via an external device such as a user handheld activator.

In some embodiments, PC may also be provided with triggers to not start or turn itself off. For example, a pacemaker system may be programmed to not enter a PC mode during certain times of the day, or provided with minimum or maximum heart rates, etc. If natural electrical conduction of the heart is present, PC may be used to override the natural conduction (one time or ongoing) or may be programmed to turn off if natural conduction is sensed. Further, internal sensors, such as activity or other physiological sensors incorporated in the pacemaker system 301, or external wireless sensor(s) 312, such as those incorporated in the pacemaker system 311, can be programmed to provide information to the system that might lead to modification or cancellation of a PC mode. For example, internal vascular or cardiac pressure sensors, internal metabolic sensors, or external EEG sensors can each contribute data to a preprogrammed set of use parameters.

A closed-loop feedback system can be used to further optimize when electrical stimulation is triggered. Outputs measured by the implantable system, for example minute ventilation, contractility, blood pressure, or intrinsic HR, could be used to adjust and test different phases of electrical stimulation during detected MSK activity.

Figure 8:
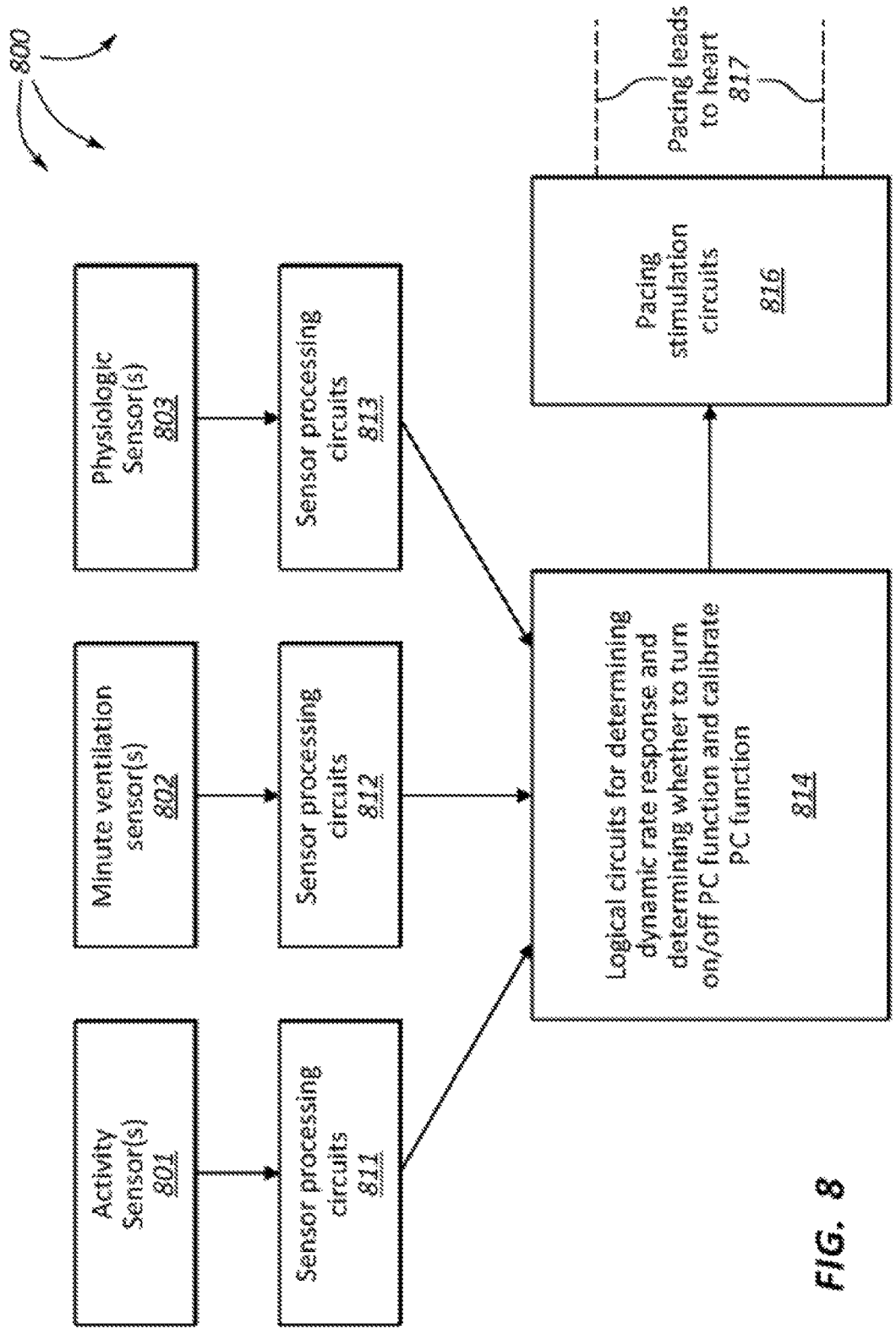
FIG. 8 illustrates an example architecture of a multi-sensor dynamic rate responsive pacing system.

As described embodiments of the invention can include multi-sensor systems. FIG. 8 illustrates an example of a multi-sensor dynamic rate responsive pacing system 800. The components of multi-sensor dynamic rate responsive pacing system 800 can be integrated into either of pacemaker systems 300 and 310 to coordinate rhythmic MSK pump timing with HR pump timing. As depicted, system 800 includes activity sensor(s) 801, minute ventilation sensor(s), and physiologic sensor(s) 803. One of more of activity sensor(s) 801, minute ventilation sensor(s), and physiologic sensor(s) 803 can be implanted in an individual and possibly integrated into a pace maker. Sensor processing circuits 811, 812, and 813 are configured to process signals from activity sensor(s) 801, minute ventilation sensor(s), and physiologic sensor(s) 803 respectively.

Output from each of sensor processing circuits 811, 812, and 813 can be sent to logic circuits 814. Logic circuits 814 (e.g., included in processor 303) can receive output from each of sensor processing circuits 811, 812, and 813. From the outputs, logic circuits 814 can determine a dynamic rate response and assess parameters that dictate the initiation, termination, calculation, or optimization of PC. Logic circuits 814 can send the dynamic rate response to pacing stimulation circuits 816 (e.g., included in pulse generator 306). Pacing stimulation circuits 816 can receive the dynamic rate response and PC from logic circuits 814. Logic circuits 814 can used pacing leads 817 to stimulate the heart in accordance with the dynamic rate response.

Figure 9:
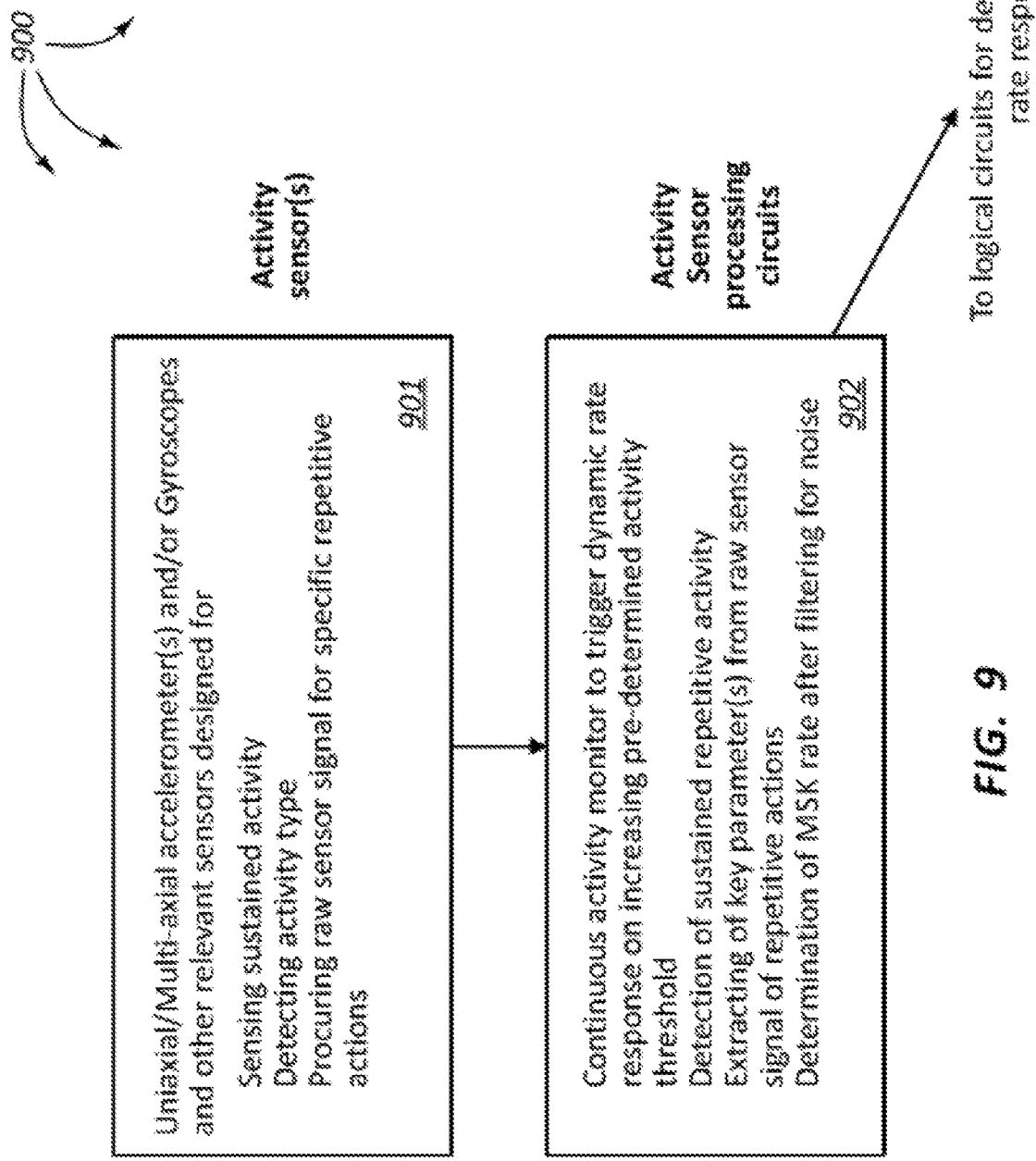
FIG. 9 illustrates an example representation of activity sensors and activity sensor processing circuits.

FIG. 9 illustrates an example representation 900 of activity sensors and activity sensor processing circuits. The activity sensors and activity sensor processing circuits in representation 900 can be integrated into either of pacemaker systems 300 and 310 to coordinate rhythmic MSK pump timing with HR pump timing. As depicted, representation 900 includes activity sensors 901 and activity sensor processing circuits 902. Activity sensors 901 can sense various different types of activity. Activity sensors 901 can indicate the different types of activity to activity sensor processing circuits 902. Activity sensor processing circuits 902 can further process data sensed by activity sensors 901 to derive various conclusions about senses activities. The conclusions can be passed to logic circuits for use in determining a dynamic rate response.

For many individuals, dependent to some extent on age, fitness level, and baseline cardiac function, natural cadences during walking and running often correlate with natural heart rates during those same activities. In fact, this natural correlation may be evolutionarily derived as the human body adapted towards an inherent capability for natural cardiolocomotor synchronization and the benefits derived from naturally occurring MCP. Therefore, embodiments of the rate responsive system are designed to be programmed to leverage the cadence of the individual during ambulation in order to identify a target paced HR, where HR=Cadence, and where the MSK pump timing at that cadence determines the cardiac stimulation timing in order to optimize PC.

Figure 10:
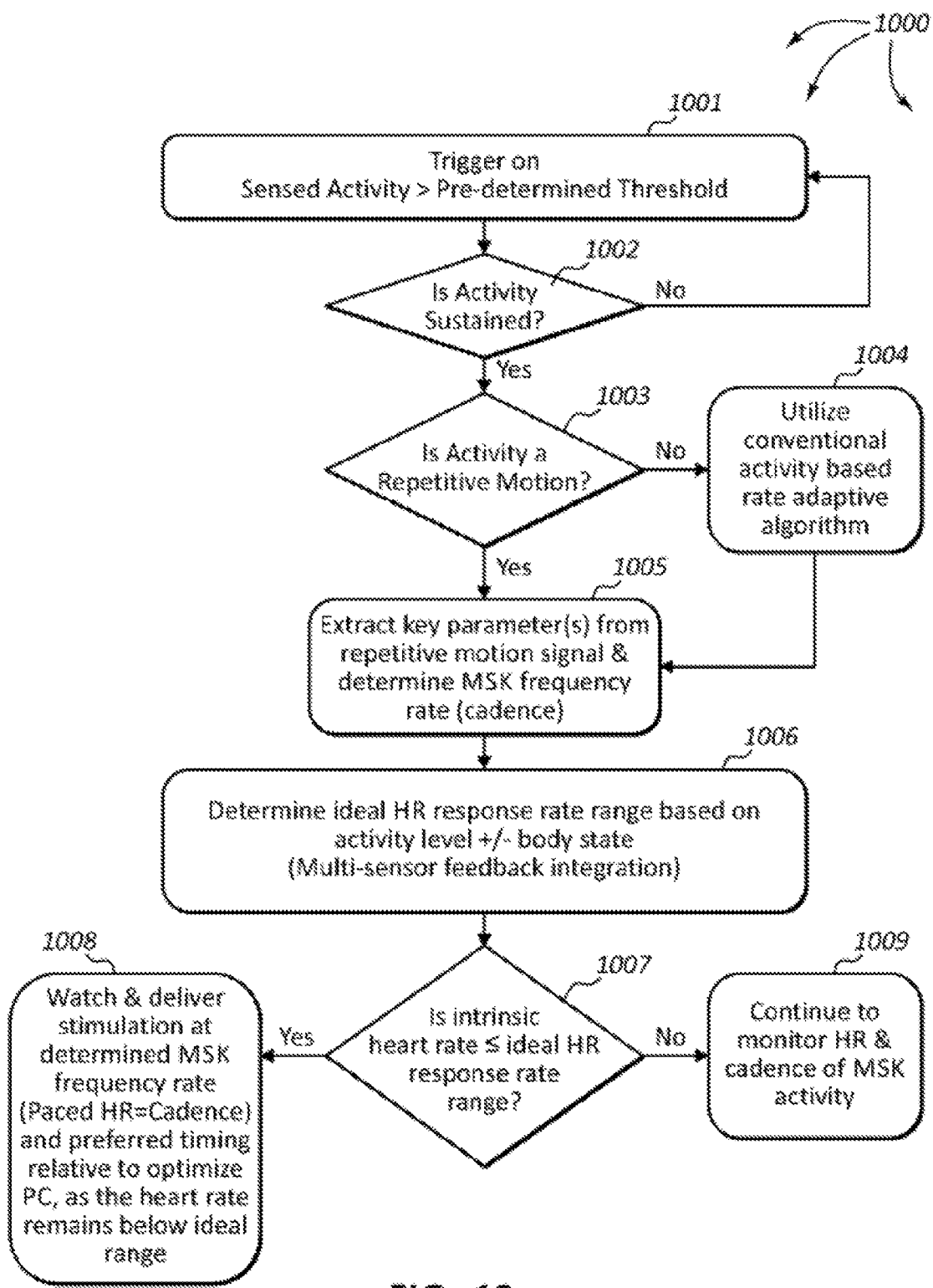
FIG. 10 illustrates a flow chart of an example method for determining ideal rate response using musculoskeletal (MSK) frequency and multi-sensor feedback.

FIG. 10 illustrates a flow chart 1000 of an example method for determining ideal rate response using MSK frequency and multi-sensor feedback. Method 1000 can be implemented in pacemaker system 300 or 301 including any of the components and functionality included in FIGS. 8 and 9.

Method 1000 includes determining if sensed activity exceeds a pre-determined threshold (1001). If so, method 1000 includes determining if the activity is continuous (decision block 1002). If the activity is not continuous (NO at decision block 1002), method 1000 returns to 1001. If the activity is continuous (YES at decision block 1002), method 1000 includes determining if the activity is a repetitive motion (decision block 1003)

If the activity is not a repetitive motion (NO at decision block 1003), method 1000 includes utilizing a conventional activity based rate adaptive algorithm (1004). If the activity is a repetitive motion (YES at decision block 1003) or after utilizing a conventional activity based rate adaptive algorithm, method 1000 includes extracting one or more parameters from a repetitive motion signal and determining an MSK frequency rate (1005).

Method 1000 includes determining if intrinsic HR is less than or equal to ideal HR response rate range (decision block 1007). If intrinsic HR is less than or equal to ideal HR response rate range (YES at decision block 1007), method 1000 includes watching and delivering stimulation at the determined MSK frequency rate and preferred timing relative to MSK pump timing to optimize PC. If intrinsic HR is not less than or equal to ideal HR response rate range (No at decision block 1007), method 1000 includes continuing to monitor HR and cadence of MSK activity.

Individuals can be provided with guidance to assist the individuals in maintaining a regular cadence or specific cadence. External devices (e.g., activity sensors(s)/transmitter(s) 312, mobile phones, etc.) can provide guidance through auditory, visual, tactile, or electrical means of instructing or prompting the user when to step (or perform some other rhythmic activity) to facilitate PC. Guidance may further encourage the user to step or otherwise activate their MSK system in ways or at rates that enable PC. An external device can receive or transmit data to an implantable pacemaker system to further coordinate counterpulsation. Other external devices, such as accelerometers, may be worn on the user and telemeter information to the pacemaker system to further increase system accuracy.

Calibrating a rate-responsive pacing system, either during the implant procedure or during subsequent physician follow-up visit, or in an automated fashion during normal physical activity might be warranted to optimally coordinate the relaxation phase of the cardiac pumping cycle to the timing of maximal MSK movement-induced blood flow. Calibration can be repeated in order to accommodate physiological changes over time, for example, optimal timing might require adjustment for changes in baseline myocardial function, such as, for example, changes related to age-dependent hardening of the vasculature, valvular disease, coronary artery disease, fluid status (e.g., hydration), hematocrit, left ventricular ejection fraction or myocardial contractility.

A static calibration technique could be performed initially during implant and with subsequent follow-up, for example, in order to analyze central arterial stiffness and pulse transit time, and accordingly adjust the delay calculations between pulse wavefront from the heart and the pulse wavefront from the MSK pump. Alternatively, more sophisticated sensor-based implementations can be leveraged to dynamically calibrate the co-ordination. Such a calibration step might include a treadmill test, wherein the patient is monitored for physiological changes during slightly different step timings relative to the cardiac contraction cycle. Exemplary changes that might be useful in determining optimal CP timing include variations in respiration or standard respiratory measures of energy metabolism (e.g. minute volume, VO2, VCO2, RER); standard measures of cardiac function (e.g. cardiac output, stroke volume, ejection fraction, contractility); tissue oxygenation (e.g. pulse oximetry), tissue or blood measures (e.g., pH, lactate, troponin) or blood pressure.

Accordingly, various embodiments of the invention facilitate the possibility of improved stamina, oxygen delivery, blood pressure, heart rate variability (marker of physical stress and health), vitality, and health benefits. Embodiments have potential application in therapeutically treating myocardial ischemia, heart failure, coronary artery disease, and other CV and circulatory issues, as well as symptoms of those diseases including angina, shortness of breath, dyspnea on exertion, arrhythmia, and premature fatigue in patients that have extrinsic cardiac pacing such as with implantable pacemakers and combination pacemaker/defibrillators.

Coordinating MSK and CV Pumping Through User Prompts (Biofeedback)

Embodiments of the invention include mechanisms for providing real-time feedback to users. The real-time feedback can help a user to voluntarily adjust or maintain the timing of their MSK activity and skeletal muscle contractions towards a target timing relationship relative to the timing of their CV pumping cycle in order to obtain and/or maintain substantially optimized hemodynamics, for example, to achieve MCP, or to achieve another targeted relationship. Real-time feedback can include a recurring guidance prompt. The guidance prompt can be adaptively responsive to actual relative MSK and CV pump timing or respective rates, and/or accuracy in achieving the target timing relationship, or maintaining this condition.

Figure 11:
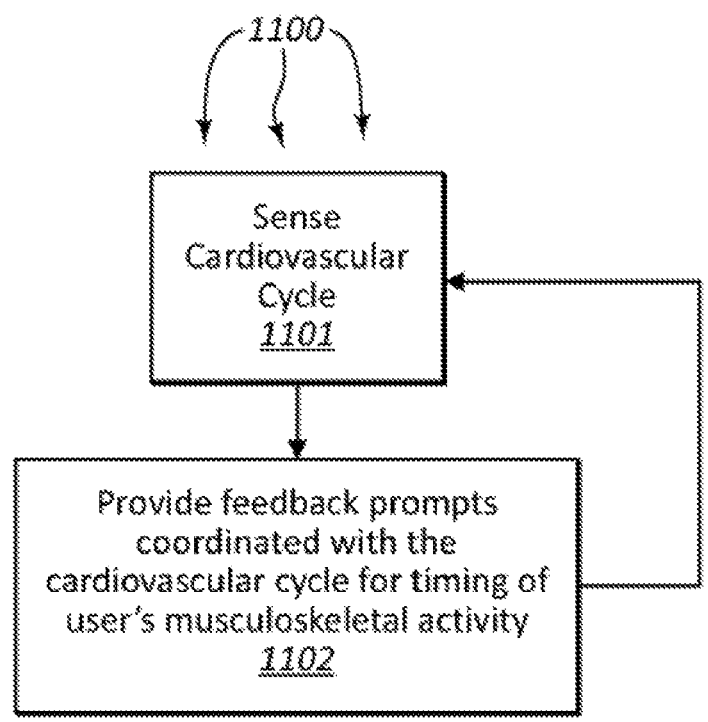
FIG. 11 illustrates a flow chart of an example method for guiding a user to obtain favorable coordination of timing between musculoskeletal and cardiovascular pumping.

FIG. 11 illustrates a flow chart of an example method 1100 for guiding a user to obtain favorable coordination of timing between musculoskeletal and cardiovascular pumping. Method 1100 includes sensing a cardiovascular cycle for individual (1101). For example, one or more sensors, such as, an ECG, a Photoplethysmogram, or an electronic auscultation sensor can be used to sense a cardiovascular cycle for an individual. The sensor(s) can be included in a device implanted in the individual (e.g., a physiological monitoring system, a drug delivery system, or a pacemaker system 301 or 311) or worn externally by the individual.

Method 1100 includes providing feedback prompts coordinated with the cardiovascular cycle for timing of the individual's musculoskeletal activity (1102). For example, a device, such as, a wearable device (e.g., a wristband), mobile device (e.g., a mobile phone), or computer system, can provide feedback prompts to the individual. The feedback prompts are provided with a timing relationship with respect to the individual's heart's contraction events. When the individual times their MSK activity to coincide with the prompts favorable MSK pump timing can be achieved.

A system can be further configured to evaluate an individual's MSK activity timing relative to the target timing by comparing data from MSK movement or muscle contraction cycle sensors (e.g., accelerometers, gyroscopes, EMG sensors, magnetic sensors, mechanical sensors, pressure sensors, cameras, radar, or electromagnetic wave based sensors) to that of CV sensors. Many forms of sensors and ways of mounting sensors to an individual are contemplated herein, including but not limited to direct skin mounting (e.g., by way of straps, adhesive), or via clothing, jewelry, mobile electronic devices, implants, cardiac pacemakers, and so on.

For activities that utilize stationary or non-stationary equipment (e.g., an exercise treadmill, elliptical, stepper, console gaming system, or bicycle), timing of an individual's MSK movements can be detected with comparable sensors to those mentioned above mounted to or integral within, or placed nearby, the equipment (e.g., accelerometer based, gyroscopic, magnetic, hall-effect, optical, magneto resistive, inductive, capacitive, rpm sensors, etc.). In order to guide the timing of the user's activity, prompts can be delivered to the individual via one or more of an auditory, visual, tactile, electrical, or other appropriate recognizable cue.

Some embodiments provide additional guidance to lead an individual to a specific cadence or a specific HR during rhythmic physical activities. For example, a system may use an audible feedback prompt to guide an individual for maintaining MCP during running. The acoustic characteristics (e.g., pitch) of the prompt can be adjusted to assist the individual. For example, the pitch of each prompt, or the pitch of one prompt in 2 or one prompt in 4, etc., can indicate the user's current HR or cadence relative to the desired HR or cadence so that the user can adjust their activity accordingly.

More specifically, a user's target HR and cadence can be set at, for example, a rate and range of 180+/−2 beats and steps per minute. When the user's HR is 175 beats per minute (below the target range), then the pitch of each nth prompt (e.g., each 4$^{th}$ prompt) could be lower than the pitch of the other 3 prompts to indicate that the HR is too low. Varying the pitch in this manner notifies the individual to increase their workload or effort in order to increase their HR and cadence (when step rate and HR are synchronized) towards the target level. An increase in work or effort can be achieved in different ways, depending on the use case. For example, in a timed run, under steady state running conditions, a longer stride length increases work output at a given cadence. In a run at a set speed (e.g. when a runner wants to remain at the speed other runners), then the work output can be increased to increase HR by other maneuvers, such as raising the knees higher with each step, or pushing higher off the ground in a more bounding step, or tensing more muscle groups with each step, or by adding isometric upper extremity contractions with each step, etc. One's ability to increase work output at a given cadence and speed may also be facilitated by the use of ambulatory exercise equipment, such as hand grip or arm or leg based motion resisting exercise devices. When the target HR is achieved, the pitch of each 4th prompt could return to same pitch as the other 3 prompts in each 4-prompt cycle. Alternatively, if the HR gets to be above the target range, the user could be notified by each 4th prompt being higher in pitch than the other 3 baseline prompts in each 4-prompt cycle. Varying the pitch in this manner notifies the individual to decrease the work or effort in order to decrease the user's HR and cadence to the target level. Other acoustic characteristics could alternatively be used (e.g., timbre, volume, duration, etc.) for audible prompts.

A wide variety of other indicators can be similarly utilized. Examples include, but are not limited to: other forms of audible prompts (e.g., a voice prompt, recorded or synthesized, indicating a desired increase or decrease in pace), a visual prompt (e.g., green for increase pace, red for decrease pace), a tactile prompt (such as a vibration or series of vibrations indicating a desired increase or decrease in pace), or a combination of two or more of such audible, visual, and tactile prompts.

In other embodiments, visual feedback is provided to the user to indicate the HR and/or cadence relative to one another and/or relative to a target value or target range. The indication of the real-time HR and movement cadence and relationship relative to each other, provides insight into how an individual can actively bring the CV and MSK pumping cycles into alignment at a chosen or provided target parameter (e.g. at a desired effort, speed, cadence, HR, etc.).

In some embodiments, visual feedback is provided to the user to indicate the HR and/or cadence relative to one another +/− relative to a target value or target range. This indication of their real-time HR and movement cadence and relationship relative to each other, provides insight into how the user can actively bring the CV and MSK pumping cycles into alignment at a chosen or provided target parameter (e.g. at a desired effort, speed, cadence, HR, etc.). As example user interfaces illustrate in FIGS. 12 and 13, when the HR and cadence are not equal, purposefully altering one or both can be leveraged to bring the HR and cadence into alignment, i.e. (1) alter cadence towards a target HR, and/or (2) alter work output (e.g. speed, stride length, effort, etc.) to effect HR changes towards a target cadence. If desired, information can be provided on the real-time relationship of both HR and cadence relative to a target value or target range.

Figure 12A:
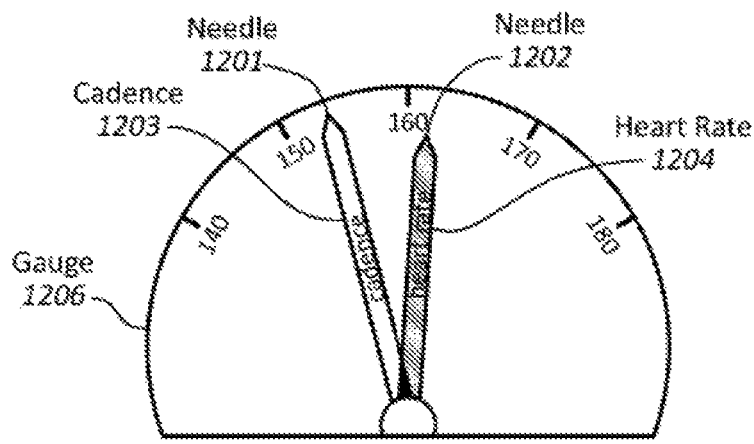
FIGS. 12A, 12B, and 12C illustrate example user interface screens of visual user prompts.
Figure 12B:
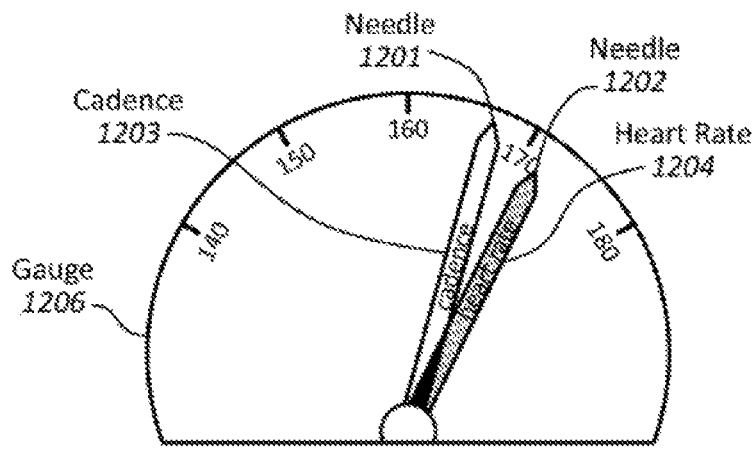
Figure 12C:
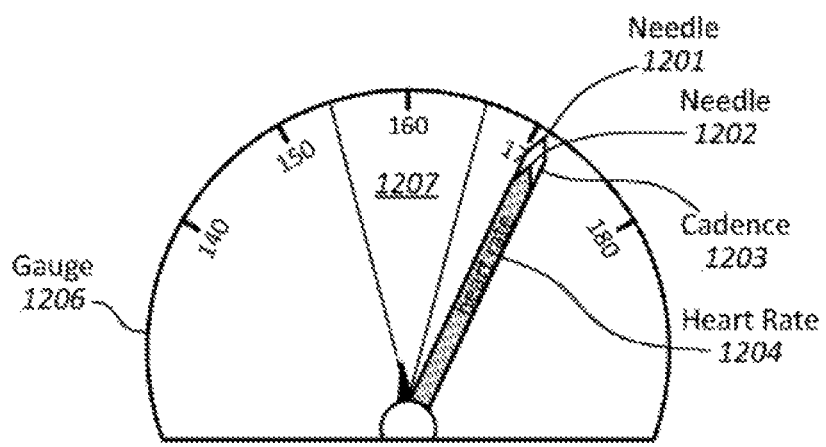

FIGS. 12A, 12B, and 12C illustrate example user interface screens of visual user prompts in the form of real-time graphical representations. FIGS. 12A, 12B, and 12C depict needles 1201 and 1202 on gauge 1206. Needles 1201 and 1202 represent rates of cadence 1203 (e.g., an individual's cadence during rhythmic MSK activity) and HR 1204 (e.g., the individual's HR during the rhythmic activity) respectively relative to one another. For the individual to achieve favorable hemodynamics, for example, MCP, needles 1201 and 1202 are to overlap (equivalently, be in alignment).

FIG. 12A depicts cadence 1203 at a lower rate than HR 1204 (i.e., that rate indicated by needle 1201 is lower rate than the rate indicated by needle 1202 on gauge 1206). Under the circumstances in FIG. 12A, the individual is being visually prompted to alter one or both of cadence 1203 and HR 1204 to bring cadence 1203 and HR 1204 (and associated needles 1201 and 1202) into alignment. That is, the individual is prompted to alter cadence 1203 towards a target heart rate, and/or (2) alter work output to effect changes to HR 1204 towards a target cadence. FIG. 12B depicts cadence 1203 still at a lower rate than, but closer to, HR 1204 (i.e., relative to FIG. 12A, the rate indicated by needle 1201 is lower than, but closer to, the rate indicated by needle 1202 on gauge 1206). Under the circumstances in FIG. 12B, the individual is still being visually prompted to alter one or both of cadence 1203 and heart rate 1204 for alignment. FIG. 12C depicts cadence 1203 and HR 1204 in alignment (i.e., needles 1201 and 1202 are in alignment). Under the circumstances in FIG. 12C, the individual is being visually prompted to maintain cadence 1203 and HR 1204 (since maintaining more favorable hemodynamics is possibly when cadence 1203 and HR 1204 are generally aligned).

When overlapped, overlapping needles can be differentiated from one another through a variety of means, including color, shape, texture or size change in the needles when they are separated and as they overlap. In one embodiment, needle 1201 is blue, needle 1202 is red, and when needles 1201 and 1202 overlap, the overlapping needles are shown in purple. A graphical representation can also indicate the current HR and cadence values relative to a target HR and target cadence value or zone of values. For example, a shaded triangular target zone 1207 can be added on gauge 1206 from HR & cadence 155 to 165 could be added in order to represent an exemplary target HR and cadence zone (shown in FIG. 12C).

As such, visual feedback can provide significant information to an individual about what needs to be done in order to ensure favorable hemodynamics (e.g., achieve MCP) at equivalent HR and cadence values. For example, if the individual can see that the HR is below the cadence, then the HR needs to be increased (work output needs to be increased) or/and the cadence needs to be decreased, and vice-versa. Alternatively, if the individual can see that the HR is noted to be below target zone 1207, work output needs to be increased to increase the HR towards the target. In yet another example, if the user can see that the cadence is above target zone 1207, but the HR is below target zone 1207, work needs to be increased to raise the HR, while the cadence needs to be decreased. In order to increase work output and HR while simultaneously lowering cadence while running on a flat surface, a user could increase running speed through an increase in stride length that is adequate to enable an overall decrease in cadence. In exemplary embodiments of a graphical interface, an individual can be reminded or directed to increase or decrease their stride length through audible or written words or symbols or other readily identifiable means of providing biofeedback to the user.

Figure 13A:
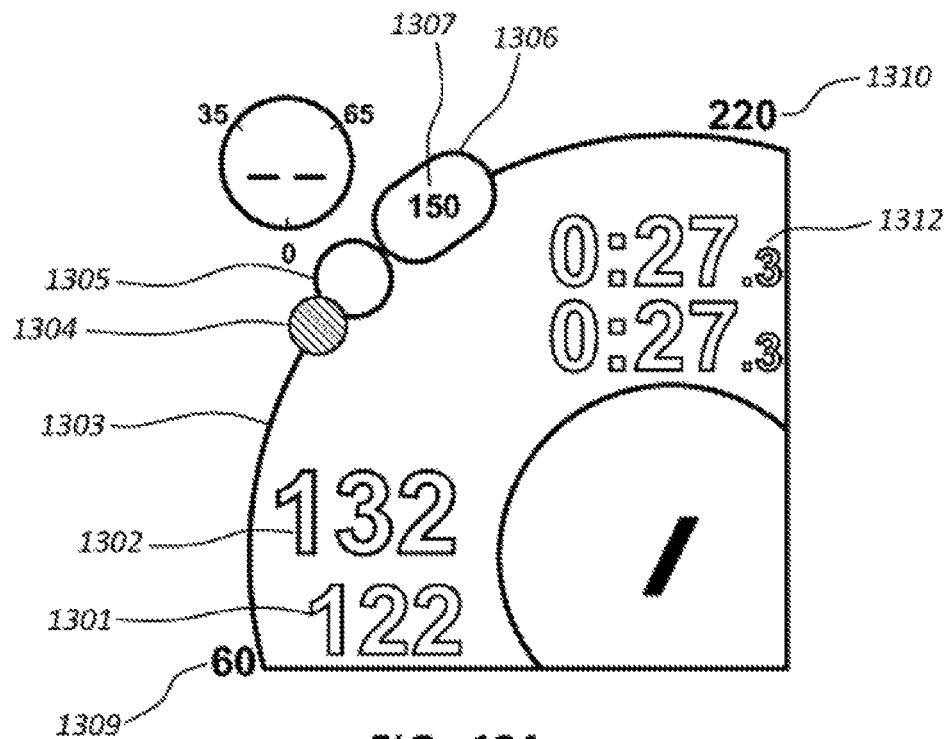
FIGS. 13A and 13B illustrate example user interface screens of visual user prompts.
Figure 13B:
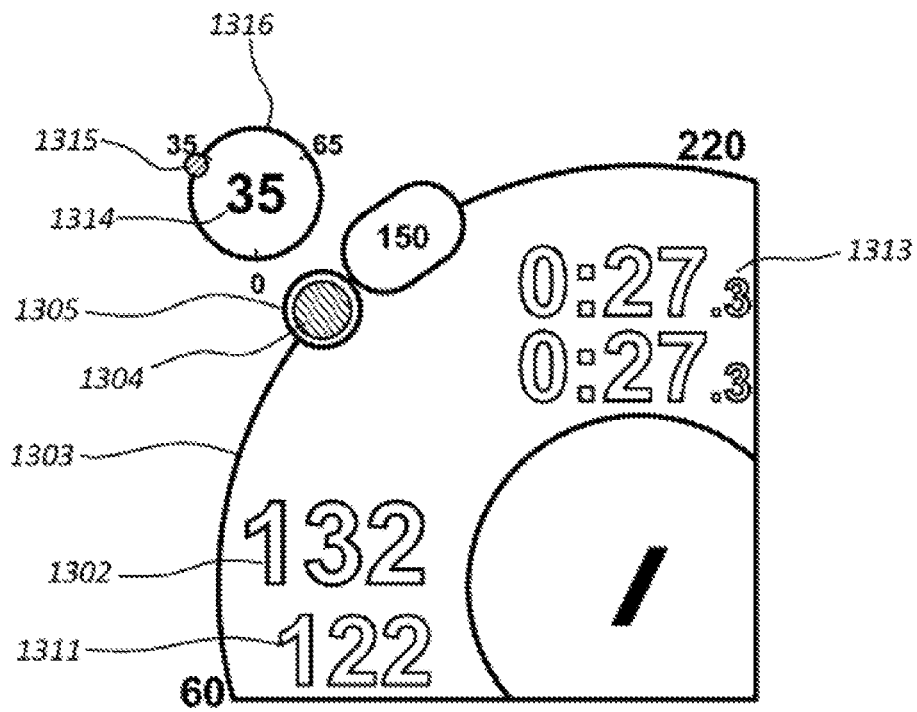

FIGS. 13A and 13B illustrate other example user interface screens of visual user prompts provided as a graphic. FIGS. 13A and 13B depict the relative rates and timing of the MSK and CV events and indicate the respective pumps' coordination. The ongoing real-time user average HR value is shown numerically in FIG. 13A by 1302, and average cadence by 1301. The user's HR and cadence are further shown graphically by shaded (alternatively, colored) circles 1305 and 1304, respectively, both located along arc 1303 that is scaled from 60 (1309) to 220 (1310) per minute. In this instance, the displayed average HR 1302 is greater than the average cadence 1301, thus the two shaded circles depict the 10/min difference in their numeric values 1302 and 1301. Also shown is shaded area 1306, indicating a target average HR and cadence band centered on a target rate value of 150 per minute (1307). The user is thus presented with a graphical indication that their cadence 1304 and HR 1305 do not match, nor does either value match the pre-defined target range shown in shaded area 1306.

FIG. 13B shows the user's sensed characteristics a short time later (per elapsed time values 1312 and 1313, shown in M:SS.s), after the user's average cadence increased to 132/min (1311), a value that now matches the average HR 1302. The graphical depiction of cadence 1304 now overlays HR 1305, as both rates share a common value. The relative timing of the MSK and CV pumps (equivalently, "phase relationship" between the MSK and CV pumps) is indicated as a value of "35" (1314), in this example using units of percent of the RR interval (% RRI), and depicted graphically as points 1315 that follow along a circular scale 1316 that spans 0-100%. Points 1315 also indicate that the MSK events are occurring at approximately 35% of the RR-interval at the time of this observation. In an alternative embodiment, one or both of the numeric timing value 1314 and graphic depiction 1315, 1316 may be eliminated.

While the example graphic interfaces shown in FIGS. 12 and 13 depict the current HR and cadence values graphically in a polar plot with needles or both located along an arc, other depictions may be used without departing from the concepts described herein. For example, the data may be presented along alternative piecewise linear and/or curvilinear profiles such as a line, ellipse, trapezoid, etc., or in side-by-side depictions for the various measures located along their own profile or set of axes. And while the figures are shown in gray-scale, color graphics may also be used.

Embodiments of the invention can be used to train individuals to achieve and experience the physical sensation of MCP. For example, the system can prompt an individual to move with and maintain a target timing, then slowly decrease the magnitude of the prompt when the system determines that accuracy of MSK pump timing relative to the target timing has been achieved and maintained for a set amount of time (e.g., some number of seconds, minutes, etc.). The prompt magnitude returns to its initial level if and when the accuracy of MSK pump timing relative to target timing diminishes (e.g., outside of some threshold).

Decreasing prompt magnitude can include decreasing the volume an audio prompt at a specified rate (while accuracy is maintained) until the prompt eventually become inaudible. The audio prompt can again become louder if and when accuracy diminishes. Decreasing prompt magnitude can also include decreasing the recurrence of presenting an audio prompt at a specified rate (while accuracy is maintained). The recurrence of presenting the audio prompt can increase if and when accuracy diminishes. For example, when an individual is running, a prompt could reversibly change from every step to every other step to every 4th step as accuracy is maintained for specified durations of time. Through practice, an individual can become increasingly capable of maintaining favorable hemodynamics (e.g., MCP) with reduced prompting. Eventually, the individual may be able to maintain favorable hemodynamics (e.g. MCP) independent of any prompts. Similar mechanisms can be used with virtually any type of prompt, including visual, tactile, electrical, or other appropriate recognizable cues.

Figure 14:
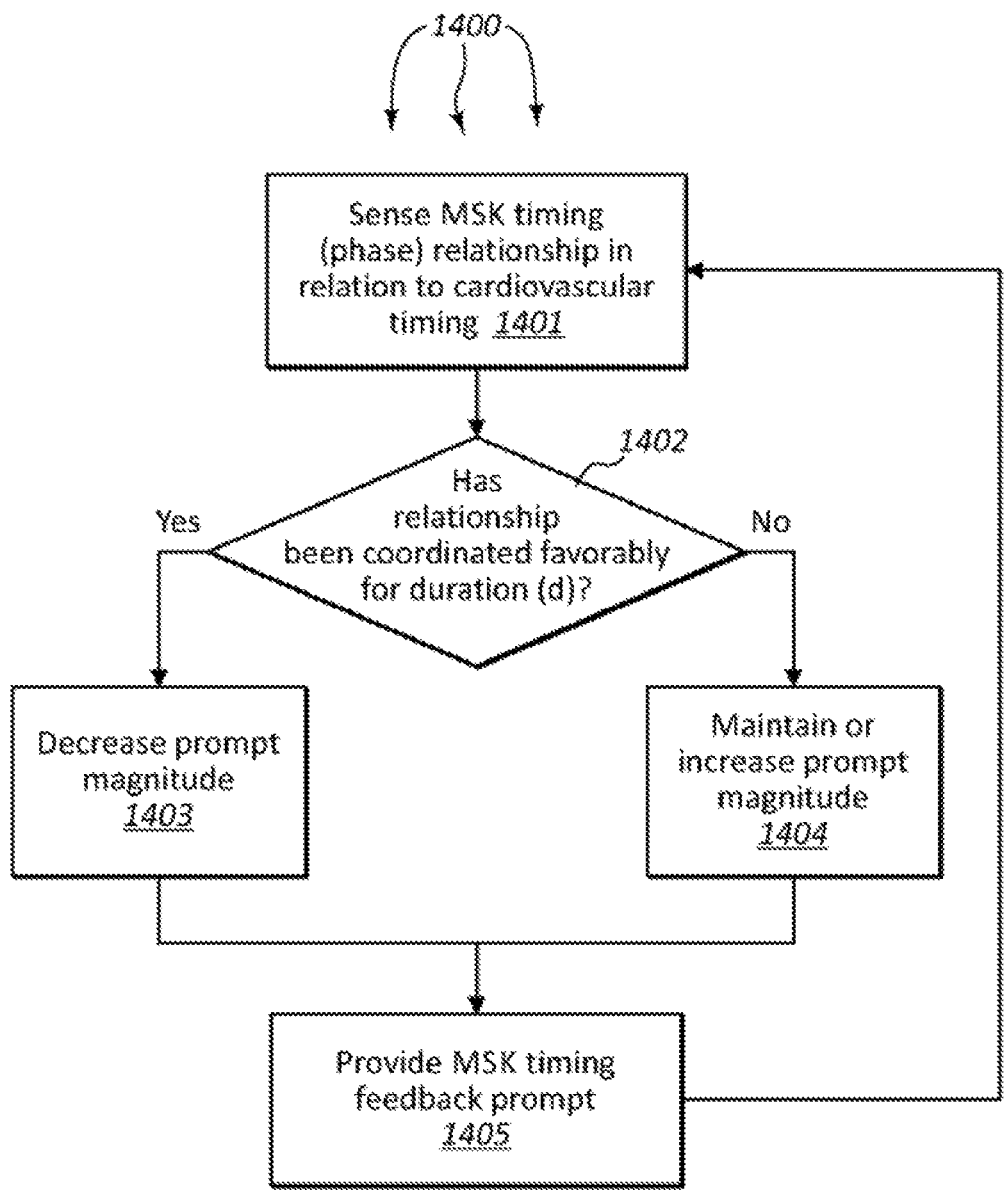
FIG. 14 illustrates a flow chart of an example method for changing prompt magnitudes to guide a user to obtain favorable coordination of timing between musculoskeletal and cardiovascular pumping.

FIG. 14 illustrates a flow chart of an example method 1400 for changing prompt magnitudes to guide a user to obtain favorable coordination of timing between MSK and cardiovascular pumping. Method 1400 includes sensing MSK timing (or equivalently phase) relationship relative to cardiovascular timing (1401). For example, a processor can process signals from one or more motion sensors and from one or more heart sensors (e.g., ECG, PPG, etc.) attached to an individual. From the processing, the processor can determine MSK pump timing relative to CV pump timing for the individual. Method 1400 includes determining if the relationship between musculoskeletal pump timing and cardiovascular pump timing has been favorably coordinated for a specified duration (decision block 1402). For example, the processor can determine if MSK pump timing relative to CV pump timing has been favorably coordinated for an individual for a specified period of time (e.g., some number of seconds, minutes, etc.). Favorably coordinated can include substantially remaining within a target relative timing range within a specified statistical measure (e.g., a defined standard deviation) of a target timing relationship or target timing relationship range. When MSK pump timing relative to CV pump timing has been favorably coordinated for the specific duration (YES at decision block 1402), method 1400 includes decreasing prompt magnitude (1403). For example, the processor can decrease the volume, brightness, frequency of presentation, etc. of a prompt. When MSK pump timing relative to CV pump timing has not been favorably coordinated for the specific duration (YES at decision block 1402), method 1400 includes maintaining or increasing the prompt magnitude (1404), up to a maximum that may be set by the user. For example, the processor can maintain or increase the volume, brightness, frequency of presentation, etc. of a prompt.

Method 1400 includes providing a musculoskeletal timing feedback prompt (1405). For example, a processor can provide a musculoskeletal timing feedback prompt in accordance with a decreased, maintained, or increased magnitude as appropriate. Appropriate can include within a range of magnitudes.

In alternative embodiments, prompts can be turned on or off as opposed to deceased or increased. A mode providing a simple on/off selection may be selected for providing or not providing a prompt during activity.

In some embodiments, auditory MSK target timing prompts are provided through music, with the beat of the music providing the target timing. The volume of the prompt beat can be increased or decreased relative to the rest of the music by the user. Alternately, the volume of the prompt beat relative to the rest of the music can be programmed to automatically increase and decrease, depending on the user's ability to initiate MSK pump activity with timing that is consistent relative to the prompt timing.

Figure 15:
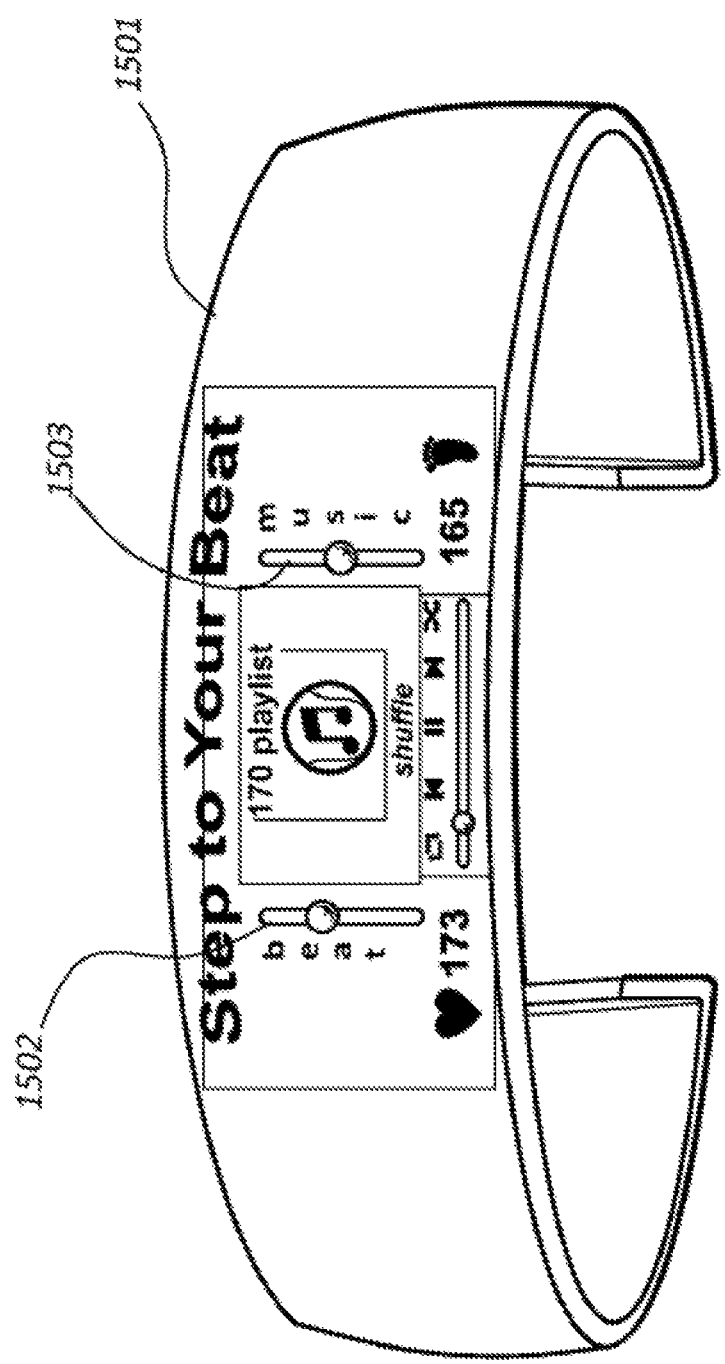
FIG. 15 illustrates an example of a wrist worn device that guides an individual to optimize the timing of rhythmic musculoskeletal.

FIG. 15 illustrates an example of a wrist worn device 1501 that guides an individual to optimize the timing of rhythmic musculoskeletal activity. By optimizing the timing of rhythmic musculoskeletal activity, the individual can achieve favorable hemodynamics, including MCP. Wrist worn device 1501 includes dual volume controls 1502 and 1503. Volume control 1502 controls volume for the beat of the music (e.g. base, drum, metronome, etc.) and volume control 1503 controls volume for the music with its normal beat volume. Dual volume controls can be useful when learning to move to a musical beat accurately, or with certain music wherein the beat of the music is less easy to discern.

Further embodiments can provide an additional prompt to an individual for timing respiration. In these further embodiments, an individual is coached to inspire or to expire with prompts similar to those used for MSK pump timing. For example, every prompt may be used for step timing when running, while the user is instructed to begin inspiration with every $4^{th}$ prompt. As such, every $4^{th}$ prompt may be provided with a different pitch than the other three prompts. In another embodiment, the volume of a breathing prompt may differ from the other prompts. In other examples, a breathing prompt with a different acoustic characteristic from the MSK activity prompts can be provided so that the user times inspiration or expiration to every $2^{nd}$, $3^{rd}$, $5^{th}$, $6^{th}$ or $7^{th}$ step, for example.

When audible characteristics of intermittent repository prompts differ from the audible characteristics of the prompts for MSK activity, the intermittent respiratory prompts can be configured to confer additional information to an individual beyond MSK activity and respiratory timing. For example, differing the pitch, duration, and volume between the intermittent and regular prompts can enable a user to distinguish among them. For example, if breathing prompts and an individual's target MSK activity timing are both desired, the differing pitch of the breathing prompt can be provided at three levels, for example, low, medium, and high frequency pitches (all differing from the stepping pitch or other characteristic). Each differing pitch prompt indicates when to breathe, while the lowest pitch indicates that the HR is below a target; a medium pitch indicates the HR is within the target range; and a high pitch that the HR is above the target rate. In another example, the audible prompts' timbre could vary in addition to or instead of varying pitch.

The training process (for MSK activity and/or respiration) can be provided in the form of a game or games. In one example, the first "level" of the game is the recording of baseline MSK pumping activity, without a prompt, but with consistency of MSK pump timing rewarded. Once that level has been completed, a higher level can include stepping accurately to a simple prompt's timing. Another higher level can include stepping accurately to a more complex prompt, such as one provided within more and more complex music as the game advances. Other optional levels include training the user and rewarding the user for accurate MSK pump timing in response to other audible, or non-audible (e.g. visual or tactile) prompts. Additional challenges in the game can include increasing the complexity of the prompted MSK activity, including a wide variety of movements or physical tasks such as walking, stomping, jumping, skipping, turning, dancing or engaging in any of an extremely wide variety of movements. Still other optional levels reward a user for continuing to maintain accurate MSK pump timing relative to cardiovascular pump timing even with the prompt no longer available to the user.

In further example embodiments of a gaming challenge, the longer the user can maintain accurate timing without or after withdrawal of an audible or visible or tactile prompt, the better the score in the game. In yet further examples, the magnitude of an MCP effect can be monitored and rewarded, for example, through the achievement of target changes in HR, tissue perfusion, respiration. BP, or blood flow, volume or pressure waves monitored by ECG, PPG, or captured in video images or other easily accessible means of physiological monitoring.

Mechanisms for providing auditory, visual, or tactile prompts to guide a individual to achieve target step timing can also be integrated with other (e.g., existing) games to enable the individual achieve favorable hemodynamics (e.g., MCP) during play. Games can leverage a variety of sensors in order to accurately characterize an individual's musculoskeletal activity and timing relative to their CC timing. Different types of MSK activity can be used to trigger, in real-time, at least one of musical notes, chords, visual feedback, and tactile sensations, while the cardiac cycle and/or respiratory cycle may trigger additional musical beats, tactile sensations, or visual feedback, guiding a user to achieve MCP through the creation of pleasant musical rhythms and sounds.

Embodiments can work with exercise gaming systems, exercise machines, or heads-up audiovisual displays. Several popular commercial games, including Dance Dance Revolution, Guitar Hero*, and Tap Tap Revenge have encouraged users to move different parts of their body in time with an audio prompt. In these commercial examples, the movement prompt is timed to correspond to the beat or notes of a specific music composition.

Figure 16C:
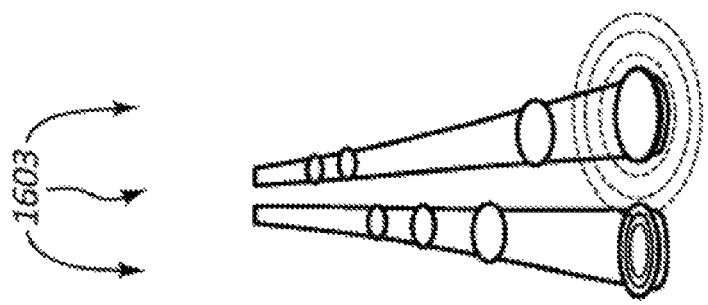
FIGS. 16A, 16B, and 16C illustrate example step sequences that can be presented to an individual when playing a game.
Figure 16B:
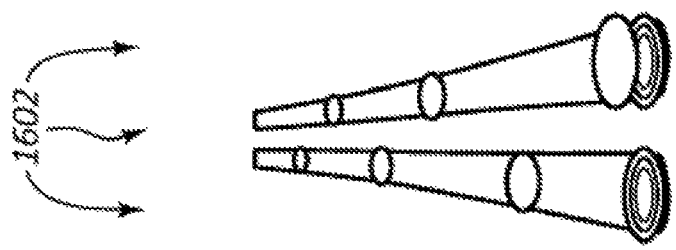
Figure 16A:
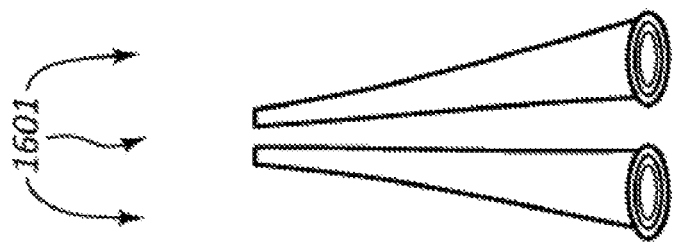

FIGS. 16A, 16B, and 16C illustrate example paired left and right foot step sequences 1601, 1602, and 1603 that can be presented to an individual when playing a game. Steps sequences 1601, 1602, and 1603 can provide feedback as to the accuracy of an individual's MSK activity timing in a fashion that provides visual cues as to what movements will be expected in the future (step sequences 1602 and 1603) as well as to the accuracy of the movement timing relative to the target timing (step sequence 1603). As illustrated in FIG. 16C, advanced levels of the game may encourage the user to step with a timing that encourages MCP but with a step sequence that includes hopping on one foot, etc. Embodiments of this type of game may leverage one or more foot-strike sensors in each shoe, foot-strike sensors in a gaming pad or deck on the floor, or video cameras in order to more accurately gauge the user's movement and movement timing. Further embodiments provide guidance to the user to move the foot or other parts of the body in different ways (e.g. step to side, slide foot, forefoot strike, tap heel, etc.) and leverage the multiple foot sensors in different parts of the shoe, or other movement sensors located elsewhere, to provide feedback as to the accuracy of those movements vs. the prompted movements.

Exercise Stress Tests

Embodiments of the invention can also be used to reduce false positives during exercise stress tests. Exercise stress tests are used to diagnose heart disease but can suffer from false positives leading to unnecessary, expensive, invasive, and risky studies and treatments. For example, stepping consistently during cardiac systole may create a temporary increase in cardiac afterload, systolic blood pressure, and HR along with a simultaneous decrease of arterial and venous blood supply to heart, even in an absence of heart disease—potentially causing ECG, ultrasound, or other monitored cardiovascular changes that can appear similar to those changes known to occur in the presence of diseased (obstructed) coronary arteries. Additionally, during a treadmill exercise stress test, leads are usually attached on skin and soft tissue, largely across the anterior and lateral torso of the patient. Thus, as the patient subsequently walks or runs on the treadmill track, the position of the leads will bounce up and down, to a degree that correlates with the stability of the soft tissue directly under the skin electrodes, repeatedly changing the position of many of these electrodes relative the position of the heart with each foot strike.

Changing these relative positions changes the measured electrical vectors in a predictable manner. As a result, stepping consistently at the same time in the heart cycle (HR=MSK cadence) can lead to motion artifacts that create a stable but distorted ECG tracing. Some of these common motion artifacts can cause false positive stress tests. When soft tissue under the chest leads is voluminous or highly mobile, as may be a more common occurrence with women than men, the larger the likelihood and magnitude of the potential movement artifact and resultant false positive incidence.

Accordingly, the timing of rhythmic physical activity relative to a monitored ECG can be further analyzed during an exercise stress test. The analysis can expose ECG changes potentially (or likely) to be related to effects of inverse iMCP (as opposed to some other cardiac condition, such as, coronary artery disease) on cardiac stress and perfusion. The analysis can also identify ECG changes that are likely to be due to motion artifacts resulting from rhythmic step timing at a consistent timing relative to the heart's cycle (and that might otherwise be indicated as a false positive for a cardiac condition, such as, heart disease).

In an additional example, a stress test system can includes separate movement monitors (e.g. accelerometers) on multiple leads, including movement monitors anchored to portions of the body that are less likely to move separately from the heart (e.g., a lead and accelerometer or accelerometer alone placed on the skin on top of the shoulder would be less likely to have the same movement artifact as a precordial lead over soft tissue on the chest wall). These separate MSK activity monitors can measure any difference in movement between the leads over soft tissue and the leads moving consistently with the heart, and can be analyzed to automatically identify or eliminate the movement artifact in the ECG tracing.

Figure 17:
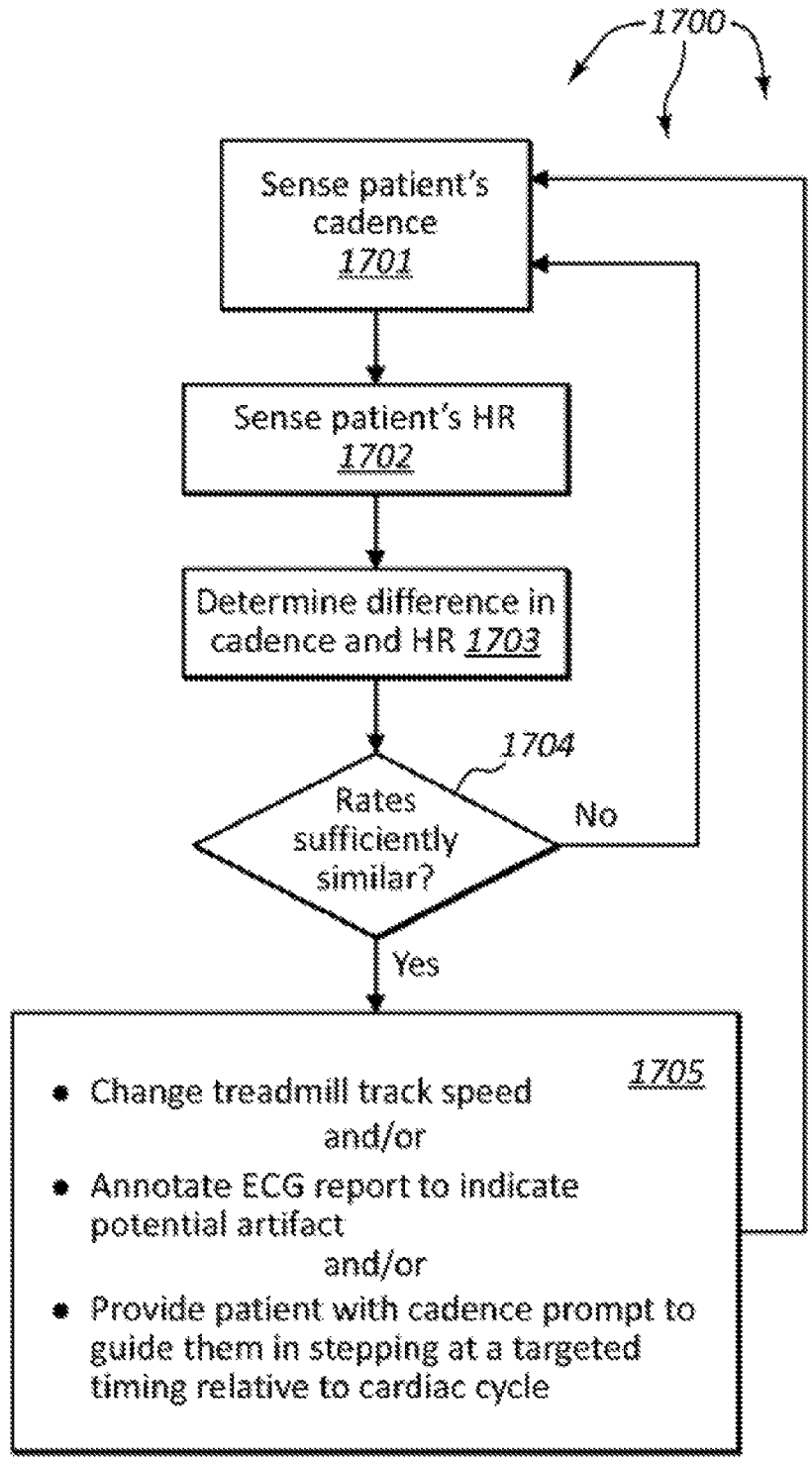
FIG. 17 illustrates a flow chart of an example method for use during an exercise stress test to reduce false positives.

FIG. 17 illustrates a flow chart of an example method 1700 for use during an exercise stress test to reduce false positives. Method 1700 includes sensing a patient's cadence (1701). For example, a processor can receive signals from one or more (e.g., activity or other described) sensors implanted in and/or externally attached to the patient, or incorporated in, attached to, or placed on the exercise equipment, or set at a distance from the patient (e.g., video camera, radar, etc). From the signals, the processor can determine the patient's cadence. Method 1700 includes sensing the patient's HR (1702). For example, a processor can receive signals from one or more heart sensors implanted in and/or externally attached to the patient. From the signals, the processor can determine the patient's HR.

Method 1700 includes determining the difference between the patient's cadence and the patient's HR (1703). For example, the processor can determine the difference between the patient's cadence and the patient's HR. Method 1700 includes determining if the patient's cadence and the patient's HR are sufficiently similar (decision block 1704). For example, the processor can determine if the patient's cadence and the patient's HR are sufficiently similar. When the patient's cadence and the patient's HR are not sufficiently similar (No at decision block 1704), method 1700 returns to 1701. That is, the patient's cadence and HR are sufficiently different, with little, if any, of the described consistent motion artifact-induced distortions present in an averaged ECG signal, and little, if any, consistent iMCP induced cardiac stress, therefore suggesting that any detected ECG changes of concern at that time are less likely to be false positives.

When the patient's cadence and the patient's heart rate are sufficiently similar (Yes at decision block 1704), and resulting movement artifacts are potentially distorting an averaged ECG signal, or, depending on the relative MSK pump timing and CV pump timing, potentially lead to ECG changes induced by iMCP, method 1700 includes one or more of: changing treadmill track speed, changing treadmill incline, annotating an ECG report to indicate a potential artifact or episode of iMCP, alerting the test administrator (e.g. visual or auditory cue to change treadmill settings or direct a change in the patient's activity), and providing a patient with a cadence prompt to guide them in stepping with a targeted cadence, or timing, relative to cardiac cycle (1705). For example, the processor (or the test administrator) can change treadmill track speed or incline, provide any of the described prompts to the patient, or annotate an ECG report for the patient. Changing treadmill track speed and/or providing prompts are remedial measures to assist the patient in stepping at a rate that differs from their HR so as to neither cause consistent distortion to their ECG signals nor cause ECG changes induced by persistent iMCP. Annotating an ECG report can enable a healthcare provider and patient to avert a possible false positive stress test. The movement artifacts may be more likely to occur in certain leads due to the axis of the heart in the individual being tested (axis as used herein means position of the heart in the chest, which can differ between individuals). Analysis of the axis is used by algorithms in embodiments of this system and method in order to more specifically identify and annotate or even potentially modify the ECG tracing in order to correct for identified movement artifacts, particularly those artifacts that are most likely to lead to the false conclusion that myocardial ischemia is present.

In alternative embodiments of an exercise stress test system and method, a healthcare provider may improve the sensitivity of a stress test by purposefully inducing iMCP. Guiding a user to "Step to the beat" with a hemodynamically unfavorable timing (e.g. foot strike during systole), or programming a pacemaker to "beat to the step" with a timing that induces iMCP, increases stress on a heart in a controlled environment by increasing myocardial work (HR & systolic blood pressure) while decreasing myocardial perfusion pressure. Because iMCP can be a naturally occurring phenomenon, a healthcare provider may find it useful to stress the heart in this fashion. One example of where this type of "extra stress" might be useful might be in testing individuals who are regularly subject to potentially dangerous or high physical stress or high risk environments, for example pilots, "at risk" athletes (e.g. with known CV conduction, structural heart, or genetic defects), firefighters, soldiers, air traffic control personnel or high level security workers. Another potential use case may be the testing of individuals who exhibit probable or possible symptoms of CV disease (e.g. angina, palpitations, syncope) during activities of daily living or normal exercise, yet show no evidence of CV disease after a standard cardiovascular medical workup. Further embodiments can include stress test protocols that compare the patient's ECG during MCP to the ECG during iMCP for further diagnostic or prognostic benefit.

Throughout the description and following claims, it should be understood that where values of HR and cadence are used, the equivalent functionality can be obtained by alternatively using R-to-R period and MSK-event-to-MSK-event periods, as each are related through their respective mathematical inverses (e.g., HR=1/RRI). Furthermore, where delay timing between MSK and CC events may be computed using time-domain methods to determine their relative timing, equivalent functionality can be achieved with methods that use the signals in their entirety, such as frequency-domain and its accompanying phase-domain computations (e.g. Fourier transforms), cross-correlation computations, and other such methods.

Figure 18:
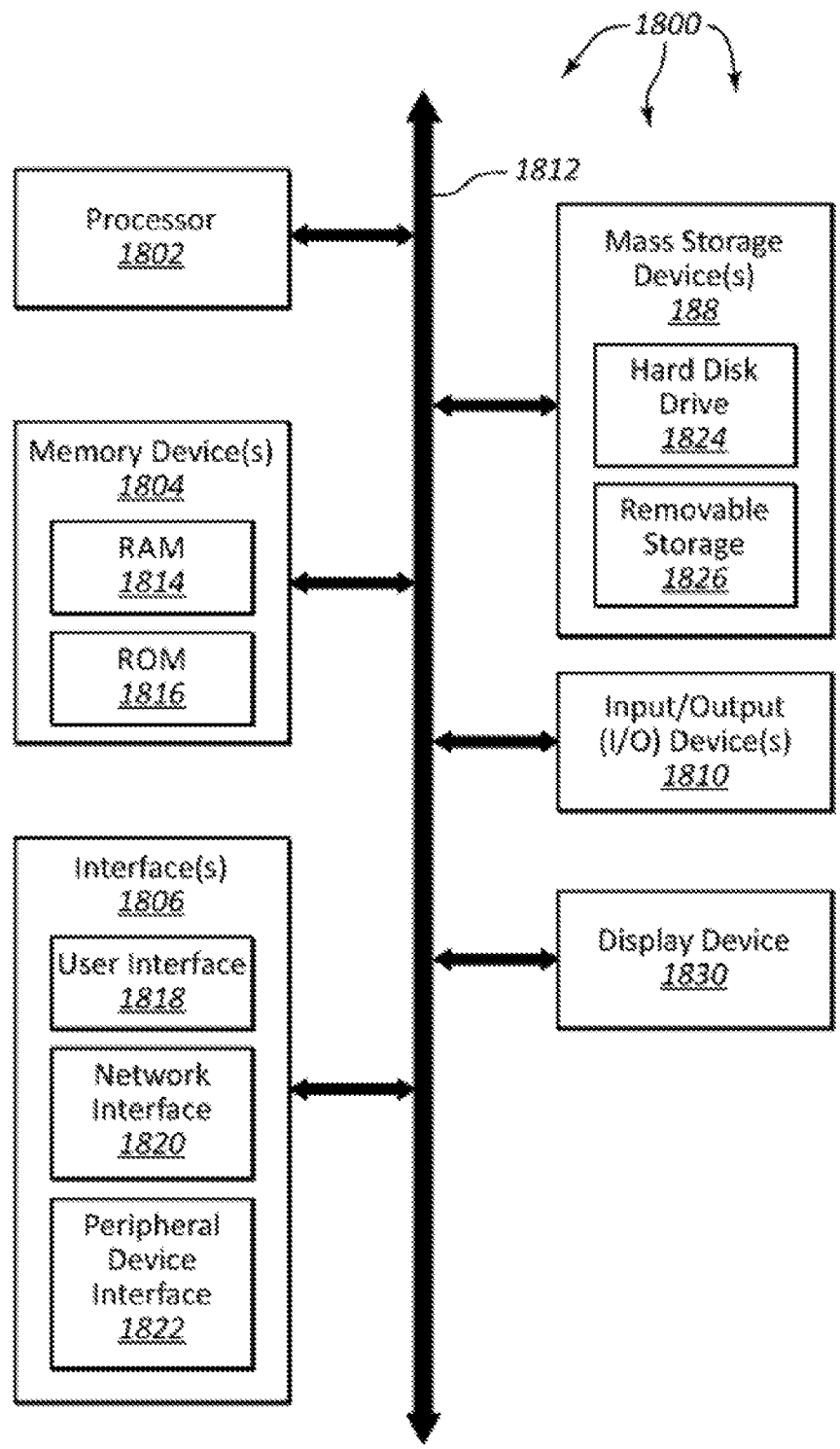
FIG. 18 illustrates an example block diagram of a computing device.

FIG. 18 illustrates an example block diagram of a computing device 1800. Computing device 1800 can be used to perform various procedures, such as those discussed herein. Computing device 1800 can function as a server, a client, or any other computing entity. Computing device 1800 can perform various communication and data transfer functions as described herein and can execute one or more application programs, such as the application programs described herein. Computing device 1800 can be any of a wide variety of computing devices, such as a mobile telephone or other mobile device, a desktop computer, a notebook computer, a server computer, a handheld computer, tablet computer and the like.

Computing device 1800 includes one or more processor(s) 1802, one or more memory device(s) 1804, one or more interface(s) 1806, one or more mass storage device(s) 108, one or more Input/Output (I/O) device(s) 1810, and a display device 1830 all of which are coupled to a bus 1812. Processor(s) 1802 include one or more processors or controllers that execute instructions stored in memory device(s) 1804 and/or mass storage device(s) 1808. Processor(s) 1802 may also include various types of computer storage media, such as cache memory.

Memory device(s) 1804 include various computer storage media, such as volatile memory (e.g., random access memory (RAM) 1814) and/or nonvolatile memory (e.g., read-only memory (ROM) 1816). Memory device(s) 1804 may also include rewritable ROM, such as Flash memory.

Mass storage device(s) 1808 include various computer storage media, such as magnetic tapes, magnetic disks, optical disks, solid state memory (e.g., Flash memory), and so forth. As depicted in FIG. 18, a particular mass storage device is a hard disk drive 1824. Various drives may also be included in mass storage device(s) 1808 to enable reading from and/or writing to the various computer readable media. Mass storage device(s) 1808 include removable media 1826 and/or non-removable media.

I/O device(s) 1810 include various devices that allow data and/or other information to be input to or retrieved from computing device 1800. Example I/O device(s) 110 include cursor control devices, keyboards, keypads, barcode scanners, microphones, monitors or other display devices, speakers, printers, network interface cards, modems, cameras, lenses, CCDs or other image capture devices, and the like.

Display device 1830 includes any type of device capable of displaying information to one or more users of computing device 1800. Examples of display device 1830 include a monitor, display terminal, video projection device, and the like.

Interface(s) 1806 include various interfaces that allow computing device 1800 to interact with other systems, devices, or computing environments as well as humans. Example interface(s) 1806 can include any number of different network interfaces 1820, such as interfaces to personal area networks (PANs), local area networks (LANs), wide area networks (WANs), wireless networks (e.g., near field communication (NFC), Bluetooth, Wi-Fi, etc., networks), and the Internet. Other interfaces include user interface 118 and peripheral device interface 1822.

Bus 1812 allows processor(s) 1802, memory device(s) 1804, interface(s) 1806, mass storage device(s) 1808, and 110 device(s) 1810 to communicate with one another, as well as other devices or components coupled to bus 1812. Bus 1812 represents one or more of several types of bus structures, such as a system bus, PCI bus, IEEE 1394 bus, USB bus, and so forth.

Although the components and modules illustrated herein are shown and described in a particular arrangement, the arrangement of components and modules may be altered to process data in a different manner. In other embodiments, one or more additional components or modules may be added to the described systems, and one or more components or modules may be removed from the described systems. Alternate embodiments may combine two or more of the described components or modules into a single component or module.

The foregoing description has been presented for the purposes of illustration and description. It is not intended to be exhaustive or to limit the invention to the precise form disclosed. Many modifications and variations are possible in light of the above teaching. Further, it should be noted that any or all of the aforementioned alternate embodiments may be used in any combination desired to form additional hybrid embodiments of the invention.

Further, although specific embodiments of the invention have been described and illustrated, the invention is not to be limited to the specific forms or arrangements of parts so described and illustrated. The scope of the invention is to be defined by the claims appended hereto, any future claims submitted here and in different applications, and their equivalents.

What is claimed:

1. A dynamic pacemaker system for artificially pacing a patient's heart, comprising:
   a musculoskeletal activity sensor for detecting a rhythmic musculoskeletal activity of a patient;
   an implantable electrical lead connectable to a heart of the patient;
   an implantable pulse generator coupled to the electrical lead and configured with the electrical lead to electrically stimulate the heart in accordance with a pacing signal; and
   an implantable processor electrically coupled to receive signals from the musculoskeletal activity sensor and to output the pacing signal to the pulse generator, wherein the processor is configured to perform a method comprising:
      detecting a recurrent aspect of the rhythmic musculoskeletal activity of the patient,
      determining a heart rate range appropriate for the patient during the rhythmic musculoskeletal activity,
      determining whether an intrinsic heart rate of the patient is within the heart rate range, and
      providing the pacing signal to the heart when the intrinsic heart rate is less than or within the heart rate range,
         wherein the pacing signal is provided at a timing which causes heart contractions in a cardiac cycle to occur with a predominantly constant timing relationship with respect to the detected recurrent aspect of the rhythmic musculoskeletal activity, the detected recurrent aspect of the rhythmic musculoskeletal activity having a consistent timing relationship with a maximal musculoskeletal blood pumping during the rhythmic musculoskeletal activity of the patient, and
         wherein the timing of the pacing signal synchronizes each instance of the maximal musculoskeletal blood pumping with a diastolic period of the cardiac cycle.

2. The dynamic pacemaker system of claim 1, wherein the processor is configured to provide the pacing signal only when the frequency of the recurrent aspect of the rhythmic musculoskeletal activity is within a pre-defined range.

3. The dynamic pacemaker system of claim 1, wherein the processor determines the timing of the pacing signal on the basis of at least one of: a percent of a step to step interval, the step to step interval being determined by the processor; a fixed time delay relative to the detected rhythmic musculoskeletal activity, wherein the fixed time delay is programmed into the processor; a calculated time after the detected rhythmic musculoskeletal activity, the time being calculated by the processor; and a calculated time before a predicted next cycle of the rhythmic musculoskeletal activity, wherein the time is calculated, and the next cycle of the rhythmic musculoskeletal activity is predicted, by the processor.

4. The dynamic pacemaker system of claim 1, wherein the pacing signal comprises electrical stimulations repeated at the timing, the timing being determined by the processor by: delivering varying pacing signals to the heart such that ventricular contraction is systematically triggered at different timing locations during a musculoskeletal pump cycle, measuring a physiological response of the patient while the pacing signals are varied, and identifying the timing that produces an optimal physiological response.

5. The dynamic pacemaker system of claim 1, wherein the musculoskeletal activity sensor comprises one or more musculoskeletal activity sensors selected from a group consisting of: a uniaxial accelerometer, a multi-axial accelerometer, a gyroscope, a magnetometer, a piezoelectric material, and a pressure sensor.

6. The dynamic pacemaker system of claim 1, wherein the musculoskeletal activity sensor comprises at least one physiologic sensor responsive to body motions, the at least one physiologic sensor selected from a group consisting of a: respiratory sensor, cardiac function sensor, motion sensor, force sensor, temperature sensor, electromyogram (EMG) sensor, electrocardiogram (ECG) sensor, electroencephalogram (EEG) sensor, and photoplethysmogram (PPG) sensor.

7. The dynamic pacemaker system of claim 1, wherein the musculoskeletal activity sensor is coupled to the implantable pulse generator and implantable in the patient.

8. The dynamic pacemaker system of claim 1, wherein the musculoskeletal activity sensor is an external wireless sensor.

9. The dynamic pacemaker system of claim 1, wherein the processor is configured to perform the method in response to: the musculoskeletal activity sensor sensing the rhythmic musculoskeletal activity, or a pre-programmed activation.

10. The dynamic pacemaker system of claim 1, further comprising a user-controlled external device, wherein the processor is configured to perform the method in response to receiving an activation signal from the user-controlled device.

11. The dynamic pacemaker system of claim 1, further comprising a metabolic sensor, wherein the processor is configured to perform the method in response to receiving a signal from the metabolic sensor indicative of an increase in metabolic demands.

* * * * *